US012740766B2

(12) United States Patent
Kirby et al.

(10) Patent No.: US 12,740,766 B2
(45) Date of Patent: Sep. 22, 2026

(54) PROCESSING AND ANALYZING ULTRASOUND SHEAR WAVE ELASTOGRAPHY IMAGES

(71) Applicant: NIKE, Inc., Beaverton, OR (US)

(72) Inventors: Brett S. Kirby, Portland, OR (US); Shannon Pomeroy, Portland, OR (US); Brad Winn, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 56 days.

(21) Appl. No.: 18/976,584

(22) Filed: Dec. 11, 2024

(65) Prior Publication Data

US 2025/0099077 A1 Mar. 27, 2025

Related U.S. Application Data

(63) Continuation of application No. 17/556,519, filed on Dec. 20, 2021, now Pat. No. 12,193,881.

(60) Provisional application No. 63/128,527, filed on Dec. 21, 2020.

(51) Int. Cl.
*A61B 8/00* (2006.01)

(52) U.S. Cl.
CPC ............ *A61B 8/485* (2013.01); *A61B 8/5207* (2013.01); *A61B 8/5292* (2013.01)

(58) Field of Classification Search
None
See application file for complete search history.

(56) References Cited

U.S. PATENT DOCUMENTS

2005/0165096 A1* 7/2005 Lee ........................ A61K 45/06 601/1
2010/0278008 A1 11/2010 Ammar
2014/0379119 A1 12/2014 Sciacchitano et al.
2019/0183461 A1 6/2019 Sonoyama
(Continued)

FOREIGN PATENT DOCUMENTS

CN 104825195 A 8/2015
CN 109003232 A 12/2018
WO 2019157486 A1 8/2019

OTHER PUBLICATIONS

Yu et al., "Evaluation of muscle damage using ultrasound imaging," (Feb. 17, 2015), J Phys Ther Sci. Feb. 17, 2015;27(2):531-534). (Year: 2015).*
(Continued)

*Primary Examiner* — Ashish S. Jasani
(74) *Attorney, Agent, or Firm* — Banner & Witcoff, Ltd.

(57) ABSTRACT

Systems and methods described herein include receiving, by a processor, one or more data files from an ultrasound shear wave elastography apparatus configured to capture viscoelastic tissue properties in an area of a subject using ultrasound shear wave electrography, processing the one or more data files to compute viscoelastic tissue parameters related to the area of the subject, compiling the viscoelastic tissue parameters and one or more associated data file identifiers to generate a processed data file, wherein the one or more associated data file identifiers includes at least one of: user characteristics, exercise characteristics, a footwear type, or an apparel type, and generating a recommendation report, wherein the recommendation report includes a footwear recommendation selected based on one or more trends from the viscoelastic tissue parameters.

20 Claims, 15 Drawing Sheets

(56) References Cited

U.S. PATENT DOCUMENTS

| | | | |
|---|---|---|---|
| 2019/0283355 | A1 | 9/2019 | Bartel |
| 2020/0000180 | A1 | 1/2020 | Sherrah |
| 2021/0145608 | A1 | 5/2021 | Herr et al. |

OTHER PUBLICATIONS

Petcu et al., "The potential of ultrasonography in the evaluation of foot orthotics therapy," (Jul. 2017), Med Ultrason 2017, vol. 19, No. 4, 416-42). (Year: 2017).*

Gennisson, J.L., et al. Continuing Education Program: Focus . . . "Ultrasound elastography: Principles and techniques", Elsevier Masson SAS, Diagnostic and Interventional Imaging (2013), 94, pp. 487-495.

Lacourpaille, L., et al. "Time-course effect of exercise-induced muscle damage on localized muscle mechanical properties assessed using elastography", ACTA Physiologica 2014, 211, pp. 135-146.

Ronneberger, O., et al. "U-Net: Convolutional Networks for Biomedical Image Segmentation", Computer Science Department and BIOSS Centre for Biological Signalling Studies, University of Freiburg, Germany, May 18, 2015, pp. 1-8, ronneber@informatik.uni-freiburg.de <mailto:ronneber@informatik.uni-freiburg.de>, <http://lab.informatik.uni-freiberg.de/.

Siracusa, J., et al. "Resting Muscle Shear Modulus Measured With ultrasound Shear-Wave Elastography as an Alternative Tool to Assess Muscle Fatigue in Humans, frontiers in Physiology", Original Research May 21, 2019, pp. 1-12.

Apr. 20, 2022—(WO) ISR & WO—App. No. PCT/US21/073044.

Bell, et al., "Measurement of intrinsic foot stiffness in minimally and traditionally shod runners using ultrasound elastography: A pilot study," (Mar. 30, 2020), Journal of Sports Sciences 2020, vol. 38, No. 13, 1516-1523, (Year 2000).

Lung, et al., "Using Elastographic Ultrasound to Assess Plantar Tissue Stiffness after Walking at Different Speeds and Durations," (Oct. 25, 2020) Appl. Sci. 2020, 10, 7498. (Year: 2020).

Bowen, Catherine, et al., "Forefoot pathology in rheumatoid arthritis identified with ultrasound may not localise to areas of highest pressure: cohort observations at baseline and twelve months," Journal of Foot and Ankle Research, Biomed Central Ltd, vol. 4, No. 1, p. 25, Nov. 23, 2011.

Liu, Jing, et al., "In Vivo Assessment of Lower Limb Muscle Stress State Based on Shear Wave Elastography," IEEE Access, IEEE, USA, vol. 8, Jul. 3, 2020, pp. 122185-122196.

* cited by examiner

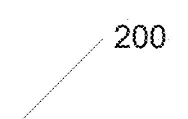
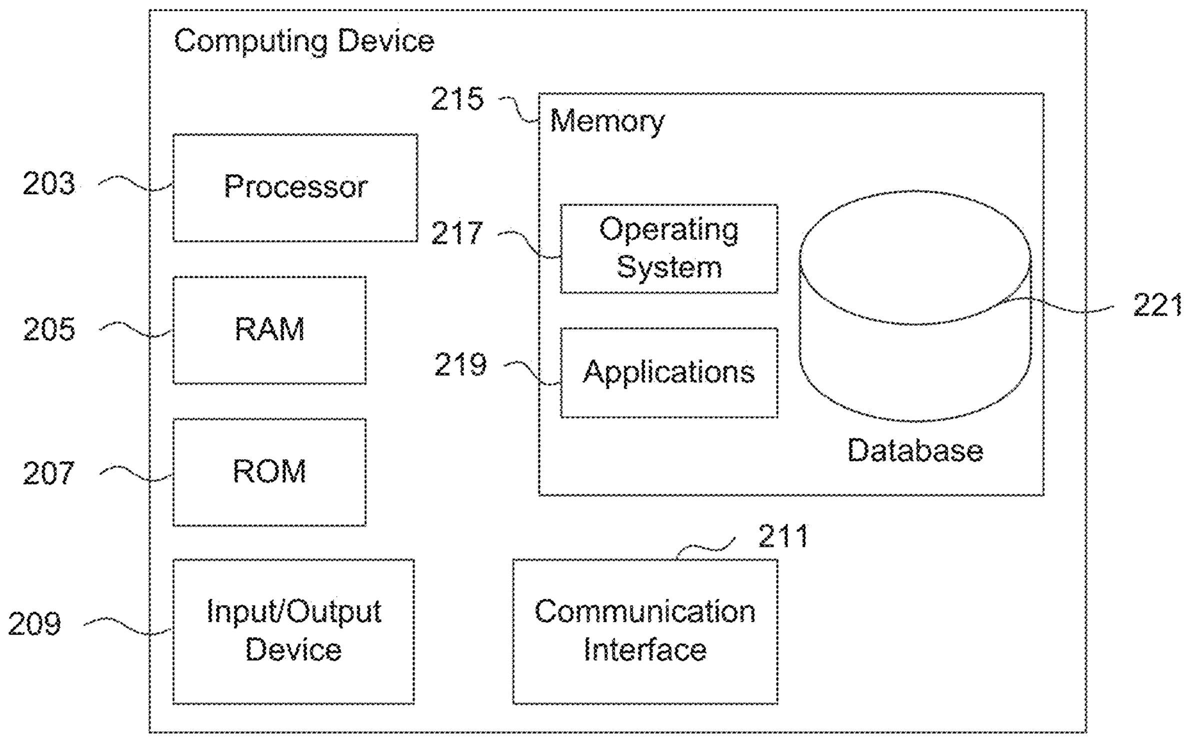
FIG. 2

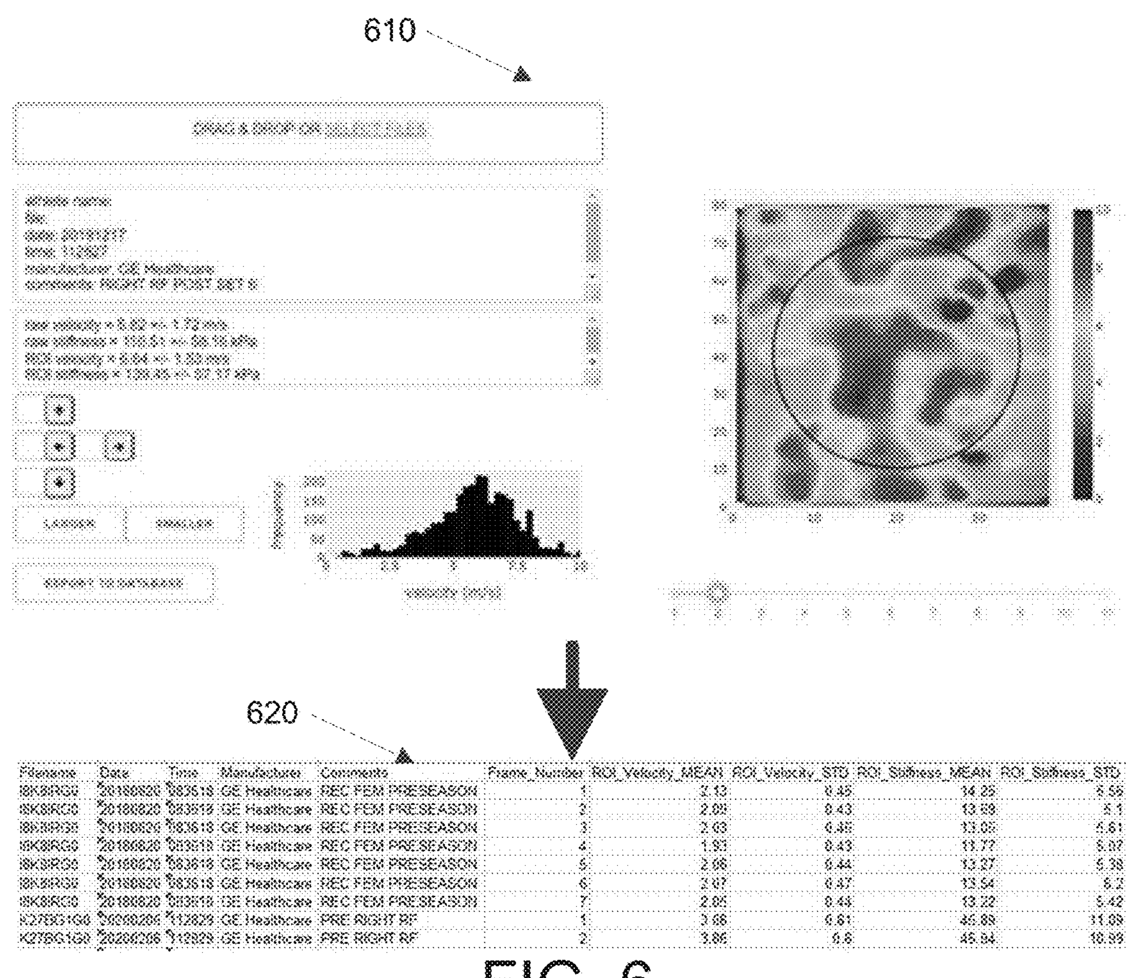

| Filename | Date | Time | Manufacturer | Comments | Frame_Number | ROI_Velocity_MEAN | ROI_Velocity_STD | ROI_Stiffness_MEAN | ROI_Stiffness_STD |
|---|---|---|---|---|---|---|---|---|---|
| I8K8RG0 | 20180820 | 083518 | GE Healthcare | REC FEM PRESEASON | 1 | 2.13 | 0.45 | 14.28 | 5.56 |
| I8K8RG0 | 20180820 | 083518 | GE Healthcare | REC FEM PRESEASON | 2 | 2.09 | 0.43 | 13.69 | 5.1 |
| I8K8RG0 | 20180820 | 083518 | GE Healthcare | REC FEM PRESEASON | 3 | 2.03 | 0.46 | 13.08 | 5.61 |
| I8K8RG0 | 20180820 | 083518 | GE Healthcare | REC FEM PRESEASON | 4 | 1.93 | 0.43 | 11.77 | 5.07 |
| I8K8RG0 | 20180820 | 083518 | GE Healthcare | REC FEM PRESEASON | 5 | 2.06 | 0.44 | 13.27 | 5.38 |
| I8K8RG0 | 20180820 | 083518 | GE Healthcare | REC FEM PRESEASON | 6 | 2.07 | 0.47 | 13.54 | 6.2 |
| I8K8RG0 | 20180820 | 083518 | GE Healthcare | REC FEM PRESEASON | 7 | 2.05 | 0.44 | 13.22 | 5.42 |
| K27BG1G0 | 20200206 | 112829 | GE Healthcare | PRE RIGHT RF | 1 | 3.68 | 0.61 | 45.89 | 11.09 |
| K27BG1G0 | 20200206 | 112829 | GE Healthcare | PRE RIGHT RF | 2 | 3.86 | 0.6 | 45.94 | 10.99 |

FIG. 6

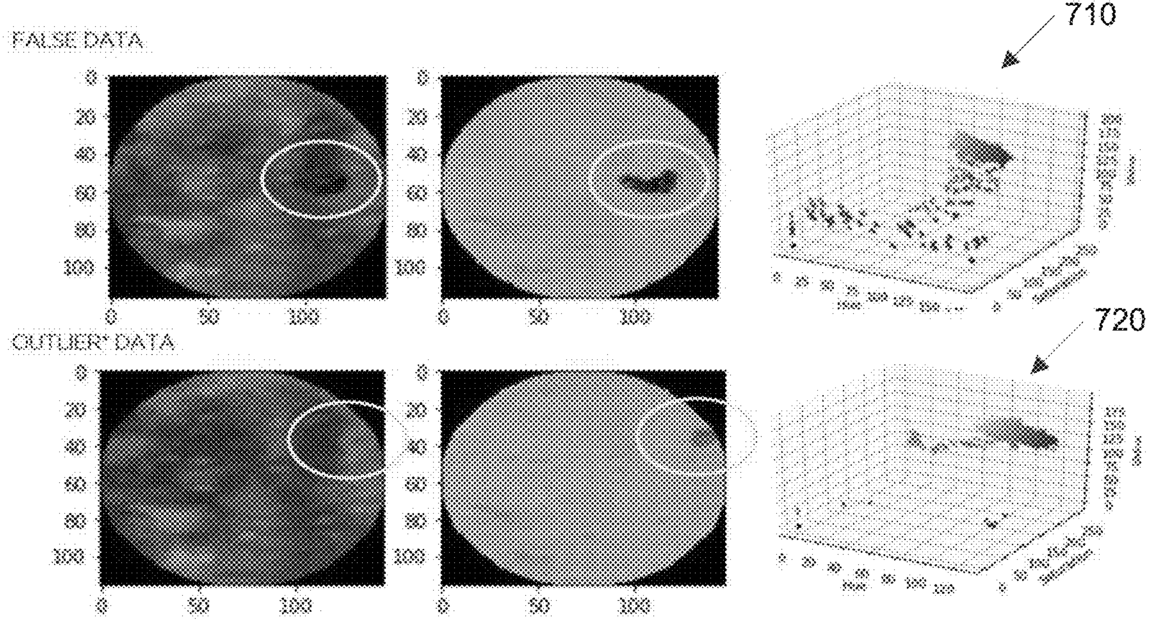

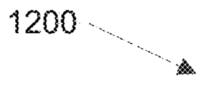
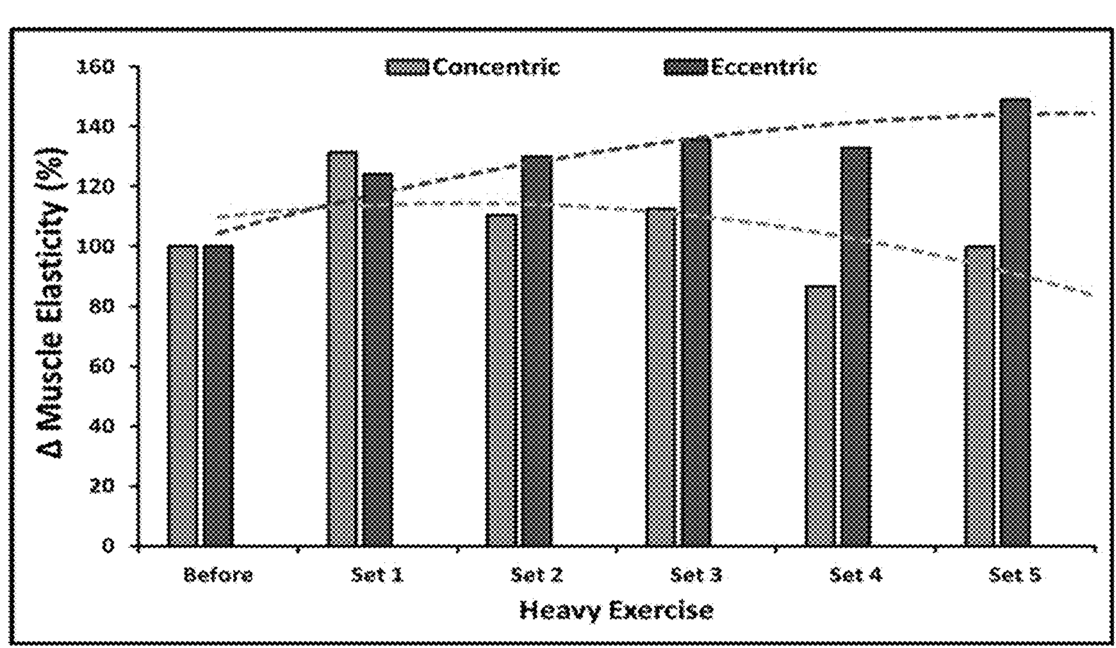
FIG. 12
1300
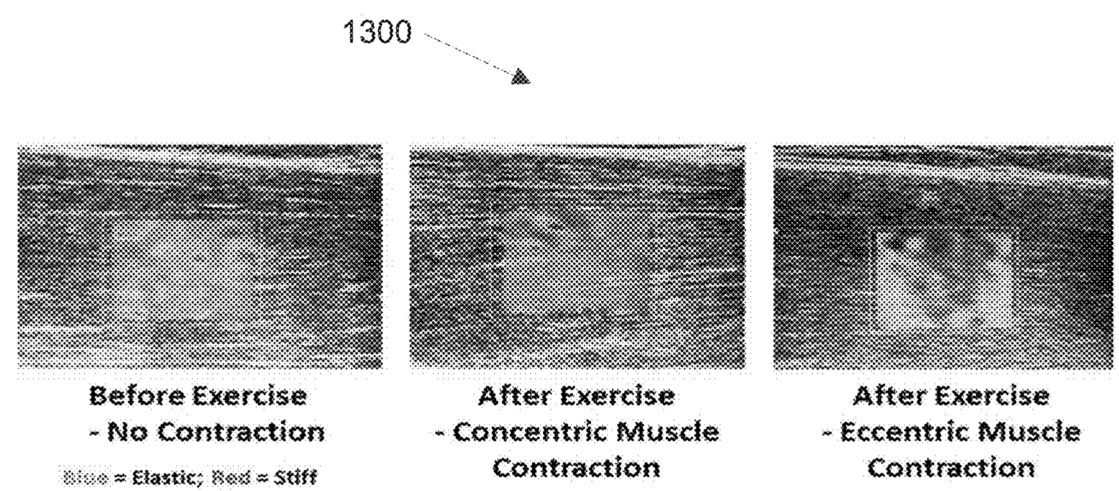
FIG. 13

1400

1500

2300

2400

PROCESSING AND ANALYZING ULTRASOUND SHEAR WAVE ELASTOGRAPHY IMAGES

CROSS-REFERENCE TO RELATED APPLICATION

This application is a continuation of U.S. patent application Ser. No. 17/556,519, filed Dec. 20, 2021, and claims the benefit of priority from U.S. Provisional Application Ser. No. 63/128,527, entitled "PROCESSING AND ANALYZING ULTRASOUND SHEAR WAVE ELASTOGRAPHY IMAGES," and filed on Dec. 21, 2020. The contents of the aforementioned applications are hereby incorporated by reference in their entirety.

TECHNICAL FIELD

Aspects of the present disclosure generally relate to systems, apparatuses, and methods for measuring, analyzing, and assessing biometric data and, more particularly, to systems, apparatuses, and methods for processing and analyzing ultrasound shear wave elastography image files.

BACKGROUND

Ultrasound shear wave elastography (SWE) may be used to noninvasively image inside the body and evaluate tissue elasticity by measuring shear wave speed. For example, some SWE apparatuses may apply an initial ultrasound pulse using acoustic radiation force, causing target area tissue to deform in response to the force of the ultrasound pulse. SWE apparatuses may thus be configured with transducers capable of generating high-voltage and long acoustic radiation force pulses. Externally induced shear waves may be achieved by compressing the tissue in a designated area, typically with a probe, and then rapidly acquiring images of the surrounding tissue. In other words, the deformation from such a pulse propagates through the tissue as one or more shear waves. These shear waves through the tissue may be monitored by additional ultrasound pulses to calculate a stiffness value of the tissue.

Tissue stiffness measurements may be useful in a number of diagnosis or monitoring applications. However, current methods for obtaining tissue stiffness measurements using SWE techniques are dependent on skilled technician targeting of regions of interest and require laborious on-machine processing of resultant images. Output from known SWE techniques is provided in a single image, without any additional interpretational context or guidance. Images taken over a range of time using known SWE techniques may be computationally and time intensive, thus limiting potential applications of SWE output.

Therefore, improved systems and methods to address these and other shortcomings in the art are desired.

SUMMARY

In light of the foregoing background, the following presents a simplified summary of the present disclosure in order to provide a basic understanding of some aspects of the disclosure. This summary is not an extensive overview of the disclosure. It is neither intended to identify key or critical elements of the disclosure nor to delineate the scope of the disclosure. The following summary merely presents some concepts of the disclosure in a simplified form as a prelude to the more detailed description provided below.

Aspects of this disclosure relate to processing and analyzing ultrasound shear wave elastography image files. In accordance with aspects of the present disclosure, apparatuses, systems, and methods described herein provide for efficient processing and analyzing of ultrasound shear wave elastography images.

According to certain aspects of the present disclosure, a method is provided that includes receiving one or more data files from an ultrasound shear wave elastography apparatus configured to capture viscoelastic tissue properties in an area of a subject using ultrasound shear wave electrography. One or more data files may processed to compute viscoelastic tissue parameters related to the area of the subject. Thereafter, viscoelastic tissue parameters may be compiled, along with one or more associated data file identifiers to generate a processed data file. The one or more associated data file identifiers may include at least one of: user characteristics, exercise characteristics, a footwear type, or an apparel type. Subsequently, a recommendation report may be generated. The recommendation report may include a footwear recommendation selected based on one or more trends from the viscoelastic tissue parameters.

In some instances, the one or more data files may include a series of ultrasound assessment files obtained over a period of time. Processing the one or more data files may include parsing image data files and batch processing the parsed image data files to obtain the viscoelastic tissue parameters. In some examples, processing the one or more data files may include calculating a mean viscoelastic tissue parameter and a standard deviation viscoelastic tissue parameter. Processing the one or more data files may include computing a stiffness-to-strain parameter from a shear wave velocity obtained via ultrasound shear wave electrography. In some instances, processing the one or more data files may include computing a quantification of muscle elasticity values of soft tissue in the area of the subject. In some examples, the viscoelastic tissue parameters may include at least one of: muscle involvement, muscle contraction, muscle elasticity, rate of muscle recovery, or muscle damage. Processing the one or more data files may include filtering one or more data files to remove noise and to compute normalized target tissue parameters.

In some aspects, an elastography report may be generated for display on a user computing device. The elastography report may include an elastography map generated based on the processed data file. The elastography map may be created based on mean viscoelastic tissue parameter values over the area of the subject. In some examples, the elastography report may include an indication of a trend in muscular elasticity in association with one or more associated data file identifiers. The elastography report may include one or more interactive elements configured to receive a user interaction. The user interaction may include editing one or more data points of the elastography map. In some instances, the user interaction may include a request for additional information relating to one or more data points of the elastography map.

In some examples, the recommendation report may include one or more interactive elements configured to receive a user interaction related to a footwear purchase process of the footwear recommendation. In some examples, the recommendation report may include an analysis summary generated based on one or more trends from the viscoelastic tissue parameters.

According to certain aspects of the present disclosure, a non-transitory computer-readable medium storage medium is provided, storing computer readable instructions that, when executed, cause a processor to perform a method. The method may include: receiving, by a processor, one or more data files from an ultrasound shear wave elastography apparatus configured to capture viscoelastic tissue properties in an area of a subject using ultrasound shear wave electrography; processing the one or more data files to obtain viscoelastic tissue parameters related to the area of the subject; compiling the viscoelastic tissue parameters and one or more associated data file identifiers to form a sequence of viscoelastic tissue parameters and one or more associated data file identifiers, wherein the one or more associated data file identifiers includes at least one of: user characteristics, exercise characteristics, a footwear type, or an apparel type; and generating a footwear recommendation based on one or more trends in the viscoelastic tissue parameters.

In certain examples, processing the one or more data files may include parsing image data files and batch processing the parsed image data files to obtain the viscoelastic tissue parameters. In some aspects, generating the footwear recommendation may include generating a report for display on a user computing device. The report may include an elastography map generated based on the sequence of viscoelastic tissue parameters and one or more associated data file identifiers and one or more interactive elements configured to receive a user interaction to edit one or more data points of the elastography map or to request additional information relating to or more data points of the elastography map.

According to certain aspects of the present disclosure, a system is provided that includes an ultrasound shear wave elastography apparatus and an electronic device. The ultrasound shear wave elastography apparatus may be configured to capture viscoelastic tissue properties in an area of a subject using ultrasound shear wave electrography. The electronic device may be in communication with the ultrasound shear wave elastography apparatus. The electronic device may include a processor and a non-transitory computer-readable storage medium storing computer-executable instructions that, when executed, cause a processor to perform a method. The method may include: receiving, by the processor, one or more data files from the ultrasound shear wave elastography apparatus; processing the one or more data files to compute viscoelastic tissue parameters related to the area of the subject; and generating a footwear recommendation based on one or more trends in the viscoelastic tissue parameters The arrangements described can also include other additional elements, steps, computer-executable instructions, or computer-readable data structures. In this regard, other embodiments are disclosed and claimed herein as well. The details of these and other aspects of the present disclosure are set forth in the accompanying drawings and the description below. Other features and advantages of the present disclosure will be apparent from the description, drawings, and claims.

BRIEF DESCRIPTION OF THE DRAWINGS

The present disclosure is illustrated by way of example and is not limited by the accompanying figures in which like reference numerals indicate similar elements and in which:

FIG. 2 illustrates a computing device in accordance with one or more aspects of the present disclosure;

FIG. 6 illustrates a data flow schematic for processing and analyzing ultrasound shear wave elastography images in accordance with one or more aspects of the present disclosure;

FIG. 7 illustrates graphical depictions of ultrasound shear wave elastography images in accordance with one or more aspects of the present disclosure;

FIGS. 9-24 illustrate various graphical depictions of ultrasound shear wave elastography image data in accordance with one or more aspects of the present disclosure.

DETAILED DESCRIPTION

Figure 1:
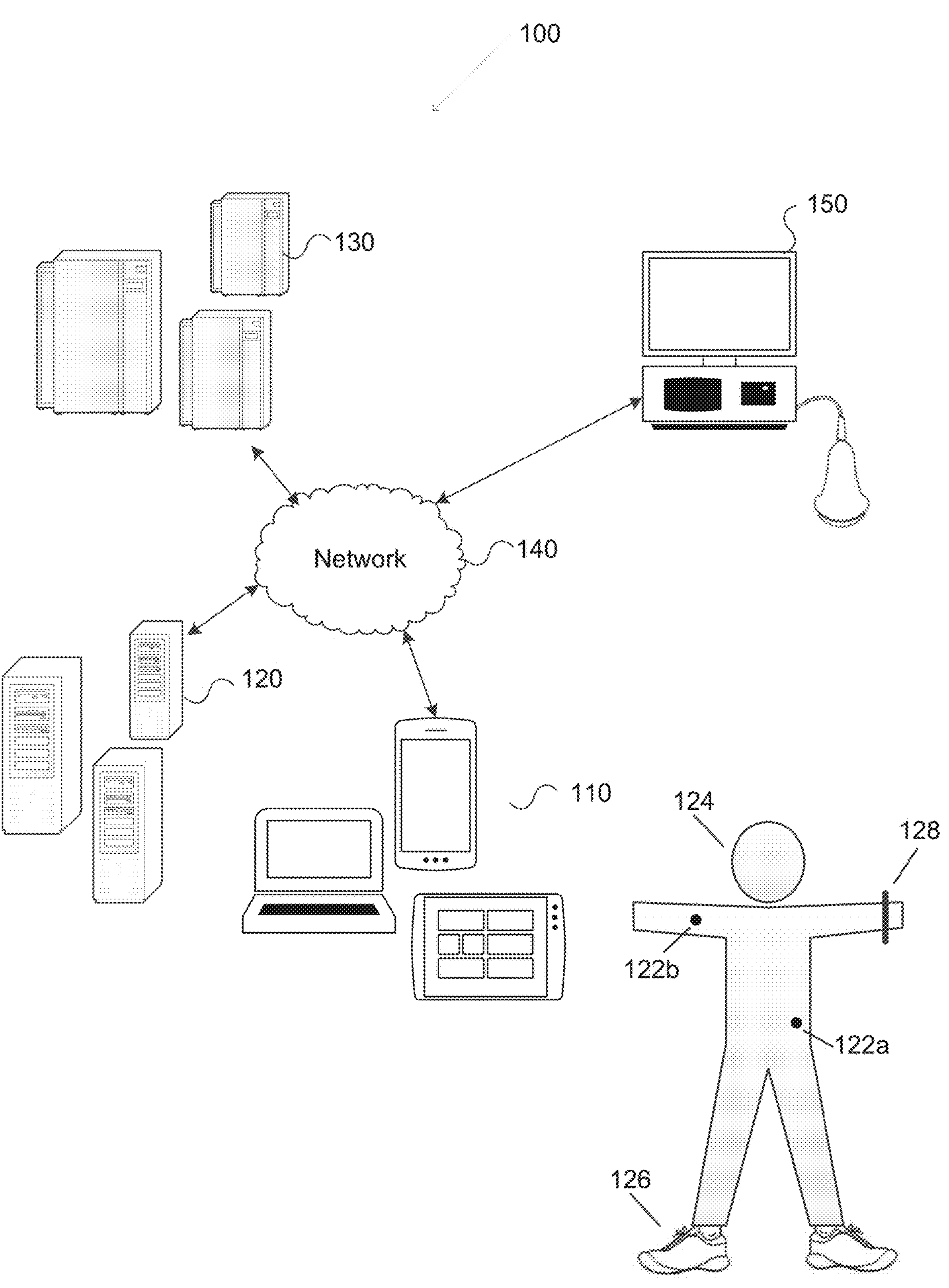
FIG. 1 illustrates an operating environment in which one or more aspects of the present disclosure may be implemented.

In the following description, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope and spirit of the present disclosure.

The following description is presented to enable one of ordinary skill in the art to make and use the aspects of the present disclosure. Reference is made to the accompanying drawings, which form a part hereof, and in which is shown by way of illustration, various embodiments of the present disclosure that can be practiced. It is to be understood that other embodiments can be utilized. Various modifications to the described embodiments will be apparent to those with skill in the art, and the general principles defined herein may be applied to other embodiments. Therefore, the present disclosure is not intended to be limited to the particular embodiments shown and described, but is to be accorded the widest scope consistent with the principles and novel features herein disclosed.

Ultrasound machines may employ shear wave elastography (SWE) capabilities to discern estimates of viscoelastic tissue properties (tissue stiffness or elasticity). These machines may employ probes that can emit and detect the velocity of transverse propagation of shear waves through the underlying tissue, and may map a shear modulus of the wave speed at a given point of interest. Current methods for obtaining SWE values require laborious on-machine processing of images as well as technician dependent targeting of regions of interest, where final SWE output is provided in a single image, without any additional interpretational context or guidance.

Certain aspects of present disclosure relate to systems, apparatuses, and methods for processing and analyzing ultrasound shear wave elastography image files. Using improved processing and analytical techniques, systems described herein may rapidly and efficiently generate ultrasound shear wave elastography image files and to quantify one or more variables from the ultrasound shear wave elastography image files.

Systems and methods for processing and analyzing ultrasound shear wave elastography image files are provided according to one or more aspects of the present disclosure. Functional ultrasound or sonography techniques provide a non-invasive means to obtain images inside the body of a subject. In an effort to discern estimates of viscoelastic tissue properties, such as tissue stiffness or elasticity, SWE capabilities may be incorporated into ultrasound machines. These ultrasound machines may include a probe capable of emitting and detecting the velocity of transverse propagation of shear waves through the underlying tissue of the subject. Shear modulus mapping of the wave speed at a given point of interest may then be provided. Final SWE imaging output may be presented with a stiffness or elasticity estimate (e.g., in kilopascals) or velocity of wave speed (e.g., meters-per-second) for a single image. However, in known methods, neither output metric provides additional interpretational context or guidance. As described here, aspects of the present disclosure address these shortcomings.

FIG. 1 illustrates an operating environment 100 in accordance with aspects of the present disclosure. The operating environment 100 may include at least one computing device 110, at least one processing server system 120, at least one recommendation server system 130, and at least one ultrasound shear wave elastography apparatus 150 in communication via a network 140. Any of the devices and systems described herein can be implemented, in whole or in part, using one or more computing systems described with respect to FIG. 2.

Computing devices 110 may receive and display ultrasound shear wave elastography data files and/or process and compile the data files as described herein. Processing server systems 120 may obtain ultrasound shear wave elastography data files, compute a variety of viscoelastic tissue properties from the data files, and/or generate processed elastography maps from the data files as described in more detail herein. Recommendation server systems 130 may generate a variety of recommendations based on models and/or preference data as described herein. Ultrasound shear wave elastography apparatus 150 may include a probe capable of emitting and detecting the velocity of transverse propagation of shear waves through the underlying tissue of the subject, and may create, store, and transmit related ultrasound shear wave elastography data files. However, it should be noted that any of the computing devices 110, processing server systems 120, recommendation server systems 130, and/or ultrasound shear wave elastography apparatus 150 may perform some or all of any step of any process as described herein. The network 140 can include a local area network (LAN), a wide area network (WAN), a wireless telecommunications network, and/or any other communication network or combination thereof.

In some aspects, one or more computing devices 110 may be configured to sense, detect, and/or measure an athletic parameter from a user, such as user 124. Examples include, but are not limited to: an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, and/or combinations thereof among others.

Ultrasound shear wave elastography apparatus 150 may be used to detect one or more viscoelastic properties of the tissue of a subject, such as user 124. In some aspects, one or more computing devices 110 may receive ultrasound shear wave elastography data files from the ultrasound shear wave elastography apparatus 150, and may store such data files in association with one or more athletic parameters received from the user 124. In that regard, user 124 may be associated with (e.g., possess, carry, wear, and/or interact with) any number of devices, such as the one or more computing devices 110, shoe-mounted device 126, and/or wrist-worn device 128. One or more devices 110, 126, 128, may be specially designed for capturing athletic data which may be analyzed in conjunction with ultrasound shear wave data files. Indeed, aspects of this disclosure relate to utilizing ultrasound shear wave data files to process and analyze such data and may provide meaningful additional interpretational context or guidance, e.g., based on analyzing the ultrasound shear wave data files in combination with athletic data or other user-specific data.

In certain embodiments, shoe-mounted device 126, and/or wrist-worn device 128 may be formed within or otherwise associated with user's 124 clothing or accessories, including a watch, armband, wristband, necklace, shirt, shoe, or the like. These devices may be configured to capture physical activity data of the user 124. It is to be understood that shoe-mounted device 126, and/or wrist-worn device 128 may detect data based on one or more athletic movements, e.g., in accordance with user interactions with the one or more computing devices 110 and/or operate independently of the one or more computing devices 110 (or any other device disclosed herein). For example, one or more devices may be configured to function as an all-day activity monitor that measures activity regardless of the user's proximity or interactions with the one or more computing devices 110. In certain embodiments, the shoe-mounted device 126 may comprise footwear which may include one or more sensors, including but not limited to those disclosed herein and/or known in the art.

In some embodiments, an example sensory location, such as elements 122*a* and 122*b*, may be associated with a physical apparatus, such as a sensor, data acquisition unit, or other device. Yet in some embodiments, an example sensory location may include a specific location of a body portion, region, or worn product that is monitored. In some embodiments, elements 122*a* and 122*b* may include sensors integrated into apparel, such as athletic clothing. Such sensors may be placed at any desired location of the body of user 124. Sensors 122*a* and 122*b* may communicate (e.g., wirelessly) with one or more devices (including other sensors).

As discussed herein, the data transferred to and from various devices in the operating environment 100 may include secure and sensitive data, such as confidential documents, user profiles, medical data, and/or procedures for developing documents. Therefore, it may be desirable to protect transmissions of such data using secure network protocols and encryption, and/or to protect the integrity of the data when stored on the various computing devices within the operating environment 100. For example, a file-based integration scheme or a service-based integration scheme may be used for transmitting data between the various computing devices. Data may be transmitted using various network communication protocols. Secure data transmission protocols and/or encryption can be used in file transfers to protect the integrity of the data, for example, File Transfer Protocol (FTP), Secure File Transfer Protocol (SFTP), and/or Pretty Good Privacy (PGP) encryption.

In some embodiments, one or more web services may be implemented within the various computing devices. Web services may be accessed by authorized external devices and users to support input, extraction, and manipulation of data between the various computing devices in the operating environment 100. Web services built to support a personalized display system may be employed cross-domain and/or cross-platform, and may be built for enterprise use. Such web services may be developed in accordance with various web service standards, such as the Web Service Interoperability (WS-I) guidelines. Data may be transmitted using the Secure Sockets Layer (SSL) or Transport Layer Security (TLS) protocol to provide secure connections between the computing devices. Web services may be implemented using the WS-Security standard, which provides for secure SOAP messages using XML encryption. Specialized hardware may be used to provide secure web services. For example, secure network appliances may include built-in features such as hardware-accelerated SSL and HTTPS, WS-Security, and/or firewalls. Such specialized hardware may be installed and configured in the operating environment 100 in front of one or more computing devices such that any external devices can communicate directly with the specialized hardware.

It will be appreciated that the network connections shown are illustrative and other means of establishing a communications link between the computers may be used. The existence of any of various network protocols such as TCP/IP, Ethernet, FTP, HTTP and the like, and of various wireless communication technologies such as GSM, CDMA, WiFi, and WiMAX, is presumed, and the various computing devices described herein may be configured to communicate using any of these network protocols or technologies.

Turning now to FIG. 2, a computing device 200 in accordance with one or more aspects of the present disclosure is shown. The computing device 200 may include a processor 203 for controlling overall operation of the computing device 200 and its associated components, including RAM 205, ROM 207, input/output device 209, communication interface 211, and/or memory 215. A data bus may interconnect processor(s) 203, RAM 205, ROM 207, memory 215, I/O device 209, and/or communication interface 211. Communication interface 211 may include one or more transceivers, digital signal processors, and/or additional circuitry and software for communicating via any network, wired or wireless, using any protocol including those described herein.

Input/output (I/O) device 209 may include a microphone, keypad, touch screen, and/or stylus through which a user of the computing device 200 may provide input, and may also include one or more of a speaker for providing audio output and a video display device for providing textual, audiovisual, and/or graphical output. In some embodiments, the I/O devices 209 may include one or more sensors and/or one or more image capture devices. The image capture devices may be used to capture images of a subject. The sensors may be used to determine viscoelastic tissue parameters in images captured using one or more image capture devices. For example, I/O device 209 may include an ultrasound shear wave elastography apparatus. Software may be stored within memory 215 to provide instructions to processor 203 allowing computing device 200 to perform various actions. For example, memory 215 may store software used by the computing device 200, such as an operating system 217, application programs 219, and/or an associated internal database 221. The various hardware memory units in memory 215 may include volatile and nonvolatile, removable and non-removable media implemented in any method or technology for storage of information such as computer-readable instructions, data structures, program modules, or other data. Memory 215 may include one or more physical persistent memory devices and/or one or more non-persistent memory devices. Memory 215 may include, but is not limited to, random access memory (RAM) 205, read only memory (ROM) 207, electronically erasable programmable read only memory (EEPROM), flash memory or other memory technology, CD-ROM, digital versatile disks (DVD) or other optical disk storage, magnetic cassettes, magnetic tape, magnetic disk storage or other magnetic storage devices, or any other medium that may be used to store the desired information and that may be accessed by processor 203.

Processor 203 may include a single central processing unit (CPU), which may be a single-core or multi-core processor (e.g., dual-core, quad-core, etc.), or may include multiple CPUs. Processor(s) 203 and associated components may allow the computing device 200 to execute a series of computer-readable instructions to perform some or all of the processes described herein. Although not shown in FIG. 2, various elements within memory 215 or other components in computing device 200, may include one or more caches, for example, CPU caches used by the processor 203, page caches used by the operating system 217, disk caches of a hard drive, and/or database caches used to cache content from database 221. For embodiments including a CPU cache, the CPU cache may be used by one or more processors 203 to reduce memory latency and access time. A processor 203 may retrieve data from or write data to the CPU cache rather than reading/writing to memory 215, which may improve the speed of these operations. In some examples, a database cache may be created in which certain data from a database 221 is cached in a separate smaller database in a memory separate from the database, such as in RAM 205 or on a separate computing device. For instance, in a multi-tiered application, a database cache on an application server may reduce data retrieval and data manipulation time by not needing to communicate over a network with a back-end database server. These types of caches and others may be included in various embodiments, and may provide potential advantages in certain implementations of document development systems, such as faster response times and less dependence on network conditions when transmitting and receiving data.

Although various components of computing device 200 are described separately, functionality of the various components may be combined and/or performed by a single component and/or multiple computing devices in communication without departing from the scope of the present disclosure.

Overview

Aspects of the present disclosure provide accelerated processing of ultrasound shear wave elastography systems and additional interpretational context and guidance related to processed ultrasound shear wave elastography data files. Targeting single images in a select region of interest using known SWE imaging techniques may not necessarily be overly assuming a capable technician can easily use on-machine software associated with the ultrasound shear wave elastography apparatus. However, with high volume serial ultrasound assessments over time (e.g., over the span of minutes, days, months, or years) and across many people and/or conditions, on-machine processing may not be possible. Aspects of the present disclosure may overcome this hurdle, e.g., with the implementation of off-line software capable of reading raw data images in rapid succession and generating SWE maps configured for further user interaction and manipulation of a region of interest (ROI) ad hoc.

Shear wave elastography systems, methods, and apparatuses described herein may quantify elasticity values of soft tissue through generation of shear waves and detection their propagation therethrough, and may subsequently use such quantified elasticity values for mapping the tissue stiffness. Such non-invasive ultrasound SWE approaches may be used for mapping human tissue stiffness or elasticity. Some known SWE application include tumor detection, obstetrics, liver and spleen stiffness, and other tissue density related diagnoses.

While quantification of viscoelastic tissue parameters may be available after imaging target tissue with an ultrasound SWE apparatus, downstream analysis and interpretation may be dependent on proficiencies of the SWE apparatus practitioner. For example, such downstream analysis and interpret may be used to guide athletic training or recovery choices and decision strategies. Use of ultrasound SWE systems and methods in accordance with the present disclosure may be employed to identify musculoskeletal soft tissue elasticity across various conditions such as, but not limited to, sex, time, injury, training loads, tissue rehabilitation, tissue fatigue, and associated force generation or resilience. Moreover, ultrasound SWE systems and methods in accordance with the present disclosure may be used to guide, for example, footwear selection strategies. Similarly, footwear selection strategies may be used to guide consequentially desired tissue elasticity changes based on studied linkages between particular selections and viscoelastic tissue parameters obtained from ultrasound SWE system and methods.

According to certain aspects of the present disclosure, a system is provided that includes an ultrasound shear wave elastography apparatus and an electronic device. The ultrasound shear wave elastography apparatus may be configured to capture viscoelastic tissue properties in an area of a subject using ultrasound shear wave electrography. The electronic device may be in communication with the ultrasound shear wave elastography apparatus. The electronic device may include a processor and a non-transitory computer-readable storage medium storing computer-executable instructions that, when executed, cause a processor to perform a method, such as process 300 of FIG. 3 or process 400 of FIG. 4.

Figure 3:
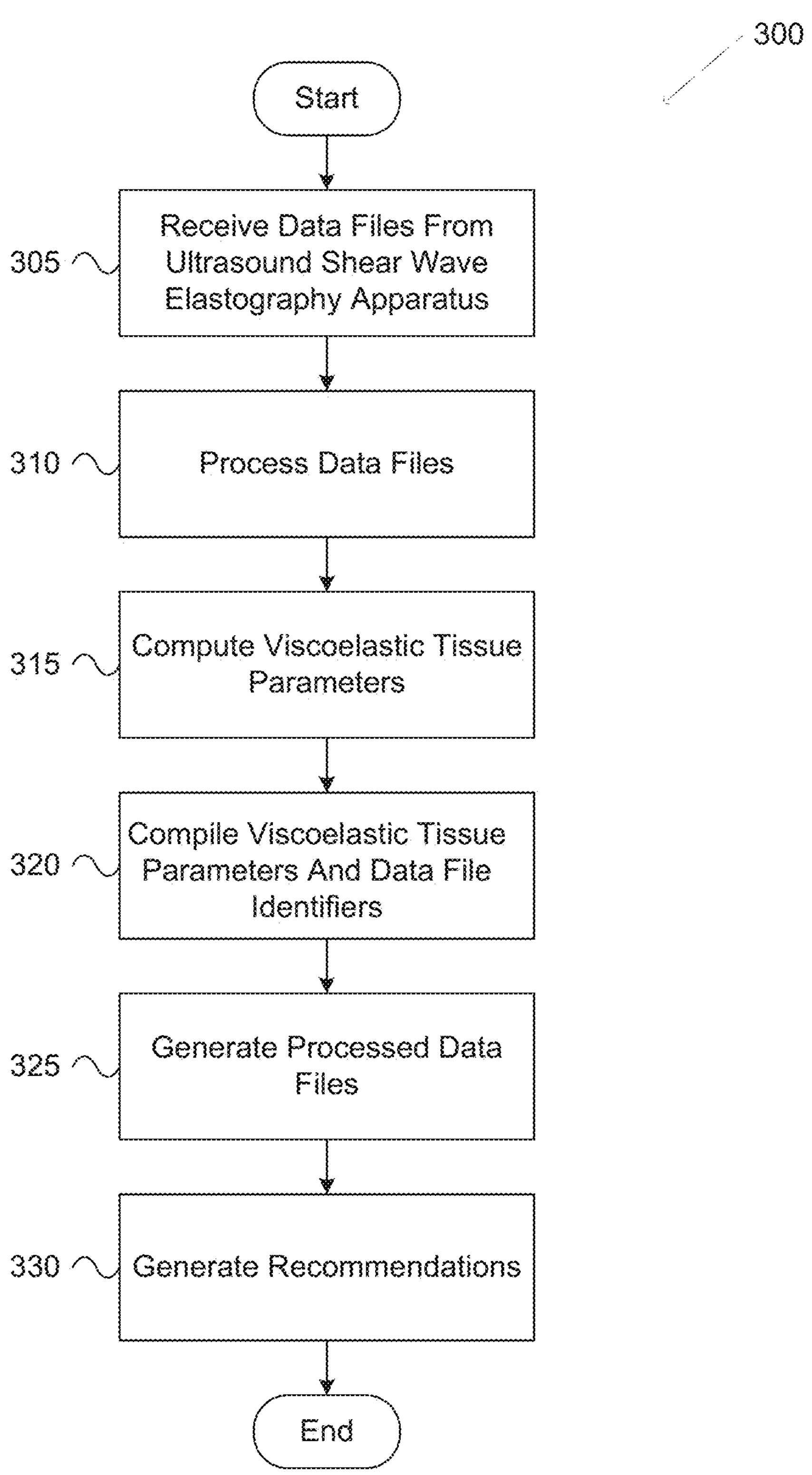
FIG. 3 illustrates a flow chart for processing and analyzing ultrasound shear wave elastography images in accordance with one or more aspects of the present disclosure.

FIG. 3 illustrates a flow chart for processing and analyzing ultrasound shear wave elastography images in accordance with one or more aspects of the present disclosure. Some or all of the steps of process 300 may be performed using one or more computing devices as described herein. In a variety of embodiments, some or all of the steps described below may be combined and/or divided into sub-steps as appropriate.

At step 305, one or more data files may be received from an ultrasound shear wave elastography apparatus configured to capture viscoelastic tissue properties in an area of a subject using ultrasound shear wave electrography. In some instances, the one or more data files may include a series of ultrasound assessment files obtained over a period of time.

At step 310, the one or more data files may be processed. Processing the one or more data files may include parsing image data files and batch processing the parsed image data files to obtain the viscoelastic tissue parameters. In some examples, processing the one or more data files may include calculating a mean viscoelastic tissue parameter and a standard deviation viscoelastic tissue parameter. Processing the one or more data files may include computing a stiffness-to-strain parameter from a shear wave velocity obtained via ultrasound shear wave electrography. In some instances, processing the one or more data files may include computing a quantification of muscle elasticity values of soft tissue in the area of the subject.

At step 315, viscoelastic tissue parameters may be computed based on the one or more data files. In some examples, the viscoelastic tissue parameters may include at least one of: muscle involvement, muscle contraction, muscle elasticity, rate of muscle recovery, or muscle damage. In some examples, the viscoelastic tissue parameters may include a quantification of muscle elasticity values of soft tissue in the area of the subject. Processing the one or more data files may include filtering one or more data files to remove noise and to compute normalized target tissue parameters.

At step 320, the computed viscoelastic tissue parameters may be compiled, along with one or more associated data file identifiers. The one or more associated data file identifiers may include at least one of: user characteristics, exercise characteristics, a footwear type, or an apparel type.

At step 325, one or more processed data files may be generated based on the compiled viscoelastic tissue parameters and the one or more associated data file identifiers. The processed data files may include filtered data files with noise remove, and with normalized target tissue parameters computed.

At step 330, a recommendation report may be generated. The recommendation report may include a footwear recommendation selected based on one or more trends from the viscoelastic tissue parameters. In some examples, the recommendation report may include one or more interactive elements configured to receive a user interaction related to a footwear purchase process of the footwear recommendation. In some examples, the recommendation report may include an analysis summary generated based on one or more trends from the viscoelastic tissue parameters.

Generating Elastography Maps

Figure 4:
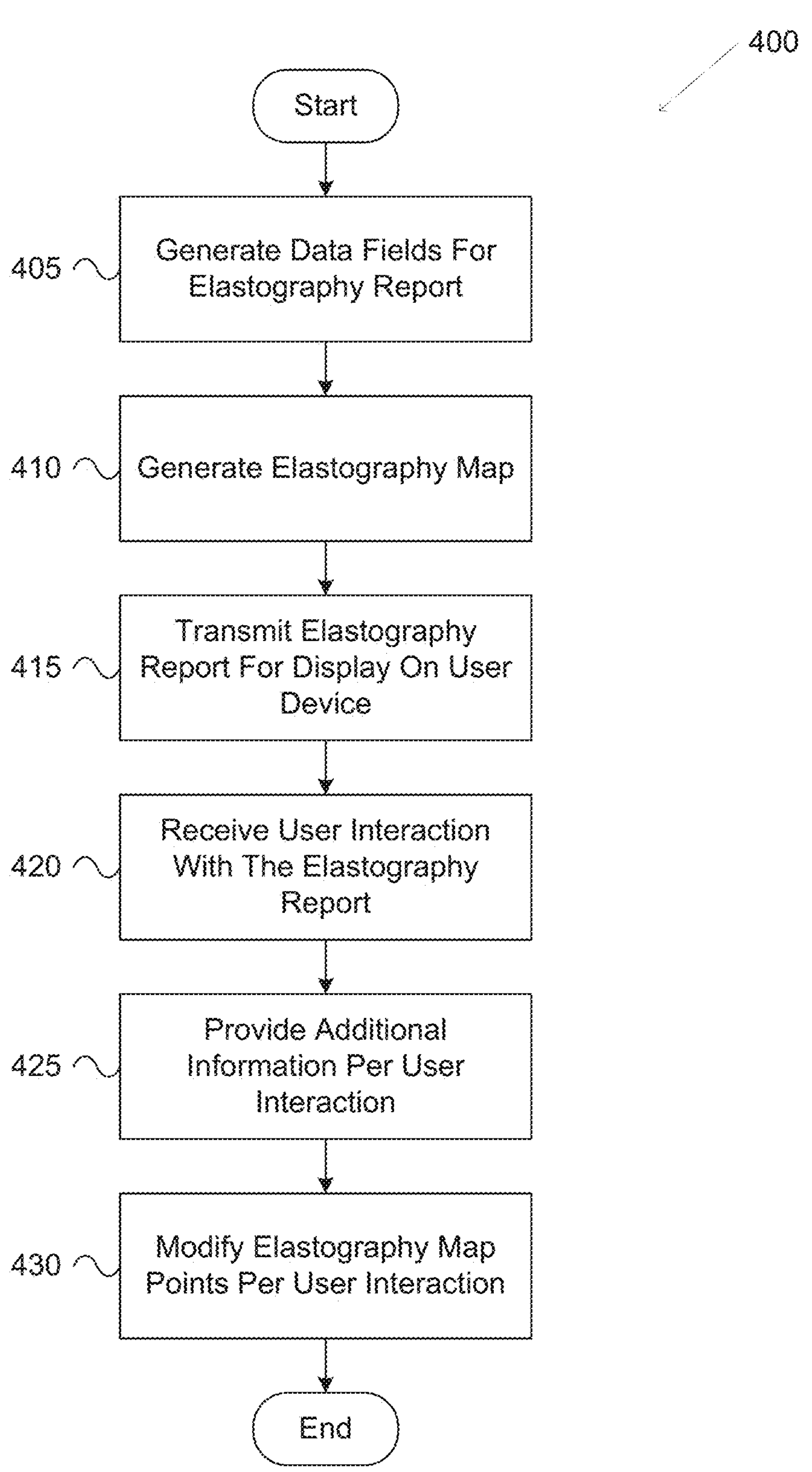
FIG. 4 illustrates a flow chart for generating interactive elastography maps from ultrasound shear wave elastography images in accordance with one or more aspects of the present disclosure.

FIG. 4 illustrates a flow chart for generating interactive elastography maps from ultrasound shear wave elastography images in accordance with one or more aspects of the present disclosure. Some or all of the steps of process 400 may be performed using one or more computing devices as described herein. In a variety of embodiments, some or all of the steps described below may be combined and/or divided into sub-steps as appropriate.

At step 405, one or more data fields for an elastography report may be generated. For example, the data fields for the elastography report may be generated upon processed data files being generated at step 325 in the process 300 of FIG. 3. In some examples, the data fields for the elastography report may be generated upon receiving one or more data files from an ultrasound shear wave elastography apparatus configured to capture viscoelastic tissue properties in an area of a subject using ultrasound shear wave electrography, processing the one or more data files to obtain viscoelastic tissue parameters related to the area of the subject, and compiling the viscoelastic tissue parameters and one or more associated data file identifiers to form a sequence of viscoelastic tissue parameters and one or more associated data file identifiers. The one or more associated data file identifiers may include at least one of: user characteristics, exercise characteristics, a footwear type, or an apparel type.

At step 410, an elastography map may be generated. For example, the elastography may be generated for display on a user computing device with the one or more data fields generated at step 405. The elastography map may be generated based on mean viscoelastic tissue parameter values over the area of the subject. In some examples, generating the elastography map at step 410 my include generating a footwear recommendation based on one or more trends in the viscoelastic tissue parameters. The elastography map may be generated based on the sequence of viscoelastic tissue parameters and one or more associated data file identifiers.

At step 415, an elastography report may be generated and transmitted for display on a user computing device. The elastography report may include an elastography map generated based on the processed data file, such as the elastography map generated at step 410. In some examples, the elastography report may include an indication of a trend in muscular elasticity in association with one or more associated data file identifiers.

At step 420, a user interaction with the elastography report may be received. In that regard, the elastography report may include one or more interactive elements configured to receive a user interaction. The user interaction may include editing one or more data points of the elastography map. In some instances, the user interaction may include a request for additional information relating to one or more data points of the elastography map. In some examples, the elastography report may include one or more interactive elements configured to receive a user interaction related to a purchase process in connection with an apparel or footwear recommendation. In some examples, the elastography report may include an analysis summary generated based on one or more trends from the viscoelastic tissue parameters.

At step 425, additional information may be provided based on a user interaction related to such additional information. In that regard, where the user interaction received at step 420 includes a request for additional information relating to one or more data points of the elastography map, that additional information may be provided at step 425.

At step 430, one or more elastography map points may be modified based on user interaction with the elastography map. In that regards, where the user interaction received at step 420 includes a request to edit one or more data points of the elastography map, those one or more data points may be edited or modified at step 430.

Figure 5:
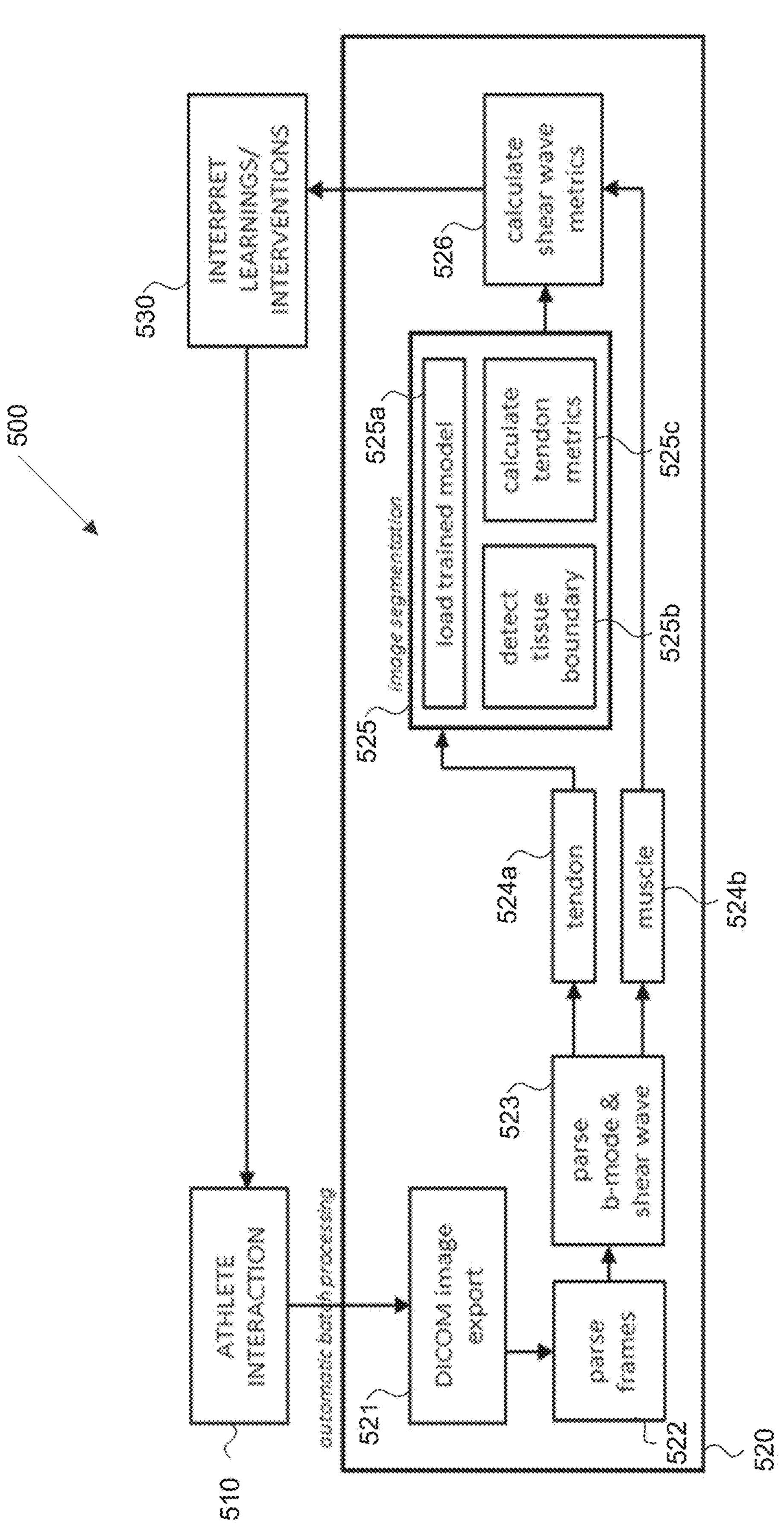
FIG. 5 illustrates a system diagram for processing and analyzing ultrasound shear wave elastography images in accordance with one or more aspects of the present disclosure.

FIG. 5 illustrates a system diagram for processing and analyzing ultrasound shear wave elastography images in accordance with one or more aspects of the present disclosure. As shown in FIG. 5, the system 500 includes athlete interaction 510, automatic batch processing 520 of ultrasound shear wave elastography images, and user interpretation for learnings and interventions 530. In certain instances, automatic batch processing 520 may receive as input athlete interaction 510, user interpretation for learnings and interventions 530 may receive as input results of the automatic batch processing, and the results of the user interpretation for learnings and interventions 530 may subsequently be used as input for further athlete interaction. In the manner, the flow of activity through the system 500 may be cyclical.

The automatic batch processing 520 of FIG. 5 may include a number of processes as part of processing and analyzing ultrasound shear wave elastography images in accordance with one or more aspects of the present disclosure. For example, subsequent to the athlete interaction 510, one or more DICOM® image exports 521 (or other similar medical image files) may be received. The system may be capable of receiving and processing the image exports 521 independent of image file formatting based on the type of ultrasound shear wave elastography apparatus that captured the associated image. In some instances, receiving and processing the image exports 521 may include receiving an export summary and/or data file identifiers or other comments related to the image files. In some examples, the automatic batch processing 520 may include batch processing multiple image files from one or more folders or other stored locations.

Thereafter, the system may parse frames 522 and parse b-mode and shear wave 523, and subsequently to identify tendon 524*a* and muscle 524*b* from the image export. Upon identifying tendon 524*a*, the system may proceed to image segmentation 525. Image segmentation 525 may include running a load trained model 525*a*, detecting tissue boundaries 525*b*, and calculating tendon metrics 525*c*. Following the image segmentation 525 of the identified tendon 524*a* and/or following identification of muscle 524*b*, the system may calculate shear wave metrics 526. For example, calculating shear wave metrics 526 may include computing mean and standard deviation values of shear wave velocities and/or stiffness/strain. The calculated shear wave metrics 526 and/or any other data, parameters, or files generated as part of automatic batch processing 520 may be sent as input for user interpretation for learnings and interventions 530. These metrics and other data may be added to a database that may bring in additional variable as relevant, such as speed, duration, type of exercise, footwear, apparel type, height, leg length, and the like.

FIG. 6 illustrates a data flow schematic for processing and analyzing ultrasound shear wave elastography images in accordance with one or more aspects of the present disclosure. As shown in FIG. 6, a dashboard 610 illustrating one or more batch processed ultrasound shear wave elastography image files is shown. As described herein, the ultrasound shear wave elastography image files may be batch processed thus resulting in a more efficient process for analyzing many image files over a period of time and/or for a plurality of subjects. The dashboard 610 may include one or more data file identifiers (e.g., subject name, file name, date, time, imaging location, subject age, subject sex, subject training program description, subject recovery program description, frame number, apparatus identification, operator identification, operator comments, and the like), and one or more viscoelastic tissue parameters (e.g., raw velocity, raw stiffness, region of interest (ROI) velocity, ROI stiffness, and the like, which may be presented an instantaneous number, mean values, standard deviation values, and the like). The dashboard 610 may also include one or more graphical depictions of the viscoelastic tissue parameters, such as a histogram of a measured viscoelastic tissue parameters, b-mode imaging graphs (a two-dimensional image representing ultrasound echoes), three-dimensional scatterplots, and the like. The processed ultrasound shear wave elastography image files and related viscoelastic tissue parameters may be imported directly into a central data location 620, such as a spreadsheet, table, data file, and the like, for the compilation of various ultrasound shear wave elastography image files and related viscoelastic tissue parameters over time and/or across different subjects.

Accordingly, such data may be processed more efficiently and compiled in a central location for subsequent analysis and interpretation. In that regard, systems and methods described herein may partially or fully automate ultrasound image processing for use in measuring muscle stiffness across multiple trials. In contrast, many current processes involve manually extraction of regions of interest from such image processing and manually recording calculated values.

Thus, system and methods described here may streamline post-processing, thereby reducing potential human error and operator time, thus enabling further applicability of ultrasound SWE technology for various analyses and learnings. Additionally, systems and methods described herein may provide improved protocols and/or processes and may create a filtering method that capable of customization in accordance with ultrasound applications and their associated sensitivities.

In accordance with various aspects of the present disclosure, post-processing of data image files may be optimized in a number of ways, including but not limited to automatically creating regions of interest, allowing for interactive checking and editing on regions of interest, removing noise, and filtering the data. As discussed, these systems and methods may provide the capability to interpret tendon and muscle from the data files, pull images into a summary, and create images of average parameter values. For example, FIG. 7 illustrates graphical depictions relating to noise removal of ultrasound shear wave elastography images in accordance with one or more aspects of the present disclosure. In that regard, systems and methods described herein may be configured to remove noise to do false data 710 as well as outlier data.

Figure 8:
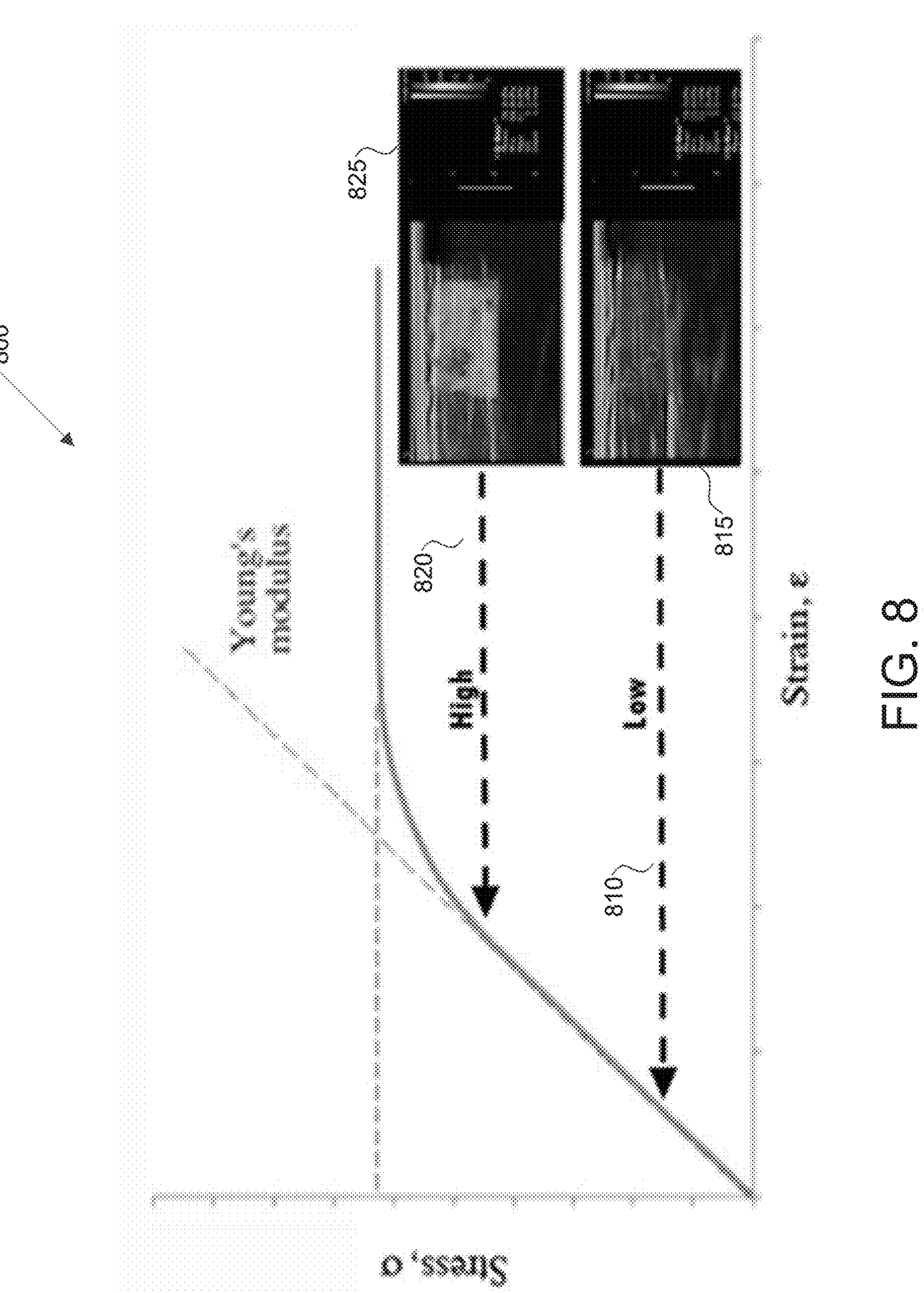
FIG. 8 illustrates a schematic stress-strain graphical depiction for ultrasound shear wave elastography images in accordance with one or more aspects of the present disclosure.

Shear wave elastography may provide quantification of absolute elasticity values of soft tissue by generating shear waves, detecting their propagation through the soft tissue, and mapping the tissue stiffness. The relation of strain to stress equates to Young's modulus, and higher or lower tissue stiffness. For example, FIG. 8 illustrates a schematic stress-strain graphical depiction for ultrasound shear wave elastography images in accordance with one or more aspects of the present disclosure. As shown in FIG. 8, a low stiffness data point 810 and corresponding low stiffness data file image 815, along with a high stiffness data point 820 and corresponding high stiffness data file image 825 are depicted.

According to certain aspects of the present disclosure, tissue identification and region of interest placement may be automated such that image data may be captured in a manner that does not depend on technician expertise, e.g., in precisely locating the ultrasound probe of a shear wave elastography apparatus prior to capturing ultrasound image data. B-mode imaging (two-dimensional ultrasound image representing ultrasound echoes) of the ultrasound shear wave elastography image data in accordance with one or more aspects of the present disclosure may enable fast and efficient visualization of anatomical structures, e.g., by not depending on a specialist to view images on shear wave elastography apparatus and place the ultrasound probe precisely in the region of interest. For instance, system and method described herein may employ algorithmic software that identifies anatomically different tissue within an ultrasound image, thus enabling rapid differentiation and interpretation of shear wave elastography values, normalized for the target tissue (e.g., such that differences in shear wave elastography values are is not due to the different tissue type itself).

According to certain aspects of the present disclosure, shear wave elastography-based output may provide outputs suitable to guide athletic decision strategies. Such applications are of increasing desirability in view of the non-invasive approach of ultrasound shear wave elastography techniques, and in view of the increasingly reliability of such techniques. While some previously known applications for shear wave elastography have primarily been limited to medical applications, such as tumor detection, obstetrics, liver and spleen stiffness, and other tissue density related diagnoses, more wide-ranging and expansive applications for shear wave elastography are possible in view of one or more aspects of the present disclosure. In particular, in addition to the viscoelastic tissue parameter obtained from shear wave elastography, systems and methods of the present disclosure may provide enhanced downstream interpretation and guidance independent of the expertise of the apparatus practitioner. In that regard, shear wave elastography may be leveraged to guide athlete choices and decision strategies.

Additionally, shear wave elastography systems and methods of the present disclosure may identify musculoskeletal soft tissue elasticity across various conditions such as, but not limited to, sex, time, exercise insult, training loads, tissue rehabilitation, and tissue fatigue and associated force generation/resilience. Moreover, ear wave elastography systems and method of the present disclosure may be used to guide, for example, for footwear selection strategies, athletic exercise modality strategies, exercise surface selection strategies, athlete tissue rehabilitation behavior strategies, athletic training program selection strategies, and the like. Similarly, such selection strategies may be used to guide consequentially desired tissue elasticity changes.

FIGS. 9-17 illustrate various graphical depictions of ultrasound shear wave elastography image data in accordance with one or more aspects of the present disclosure.

Figure 9:
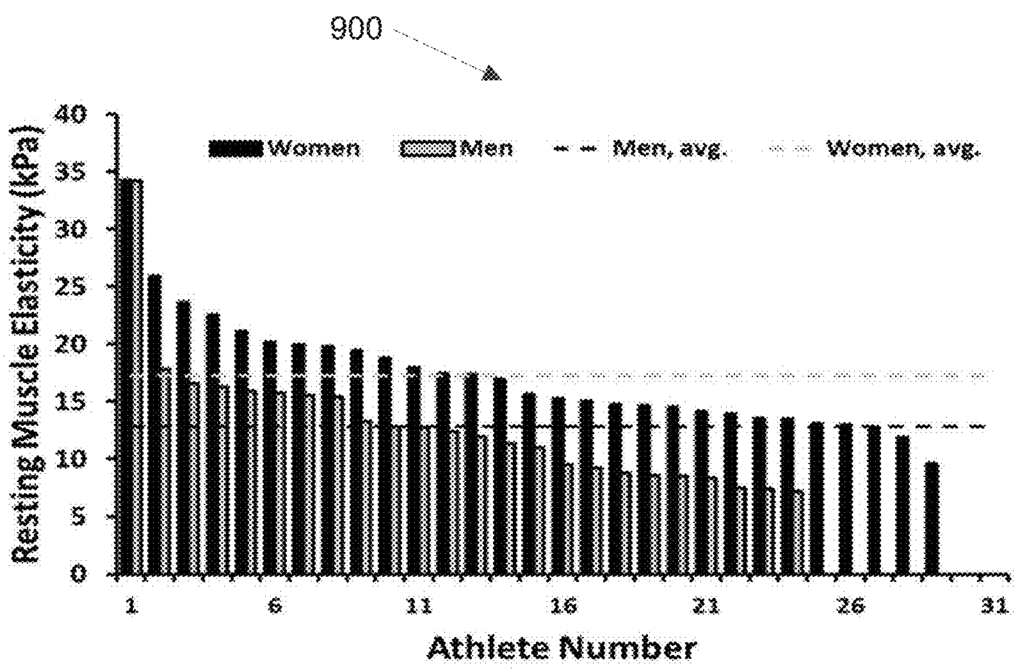
Figure 10:
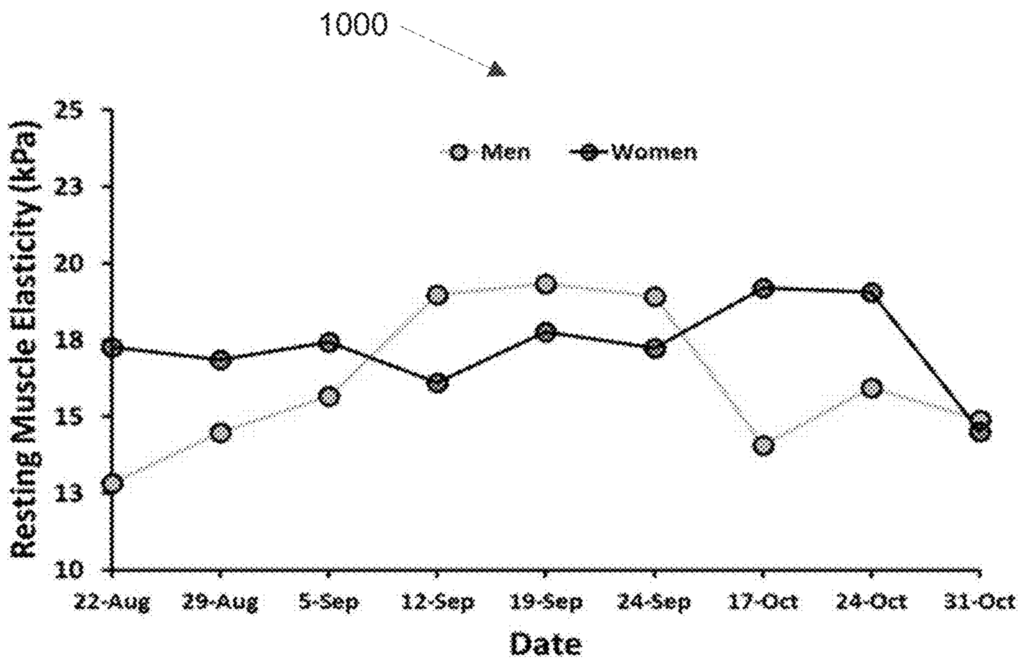

As shown in FIGS. 9 and 10, shear wave elastography systems and methods of the present disclosure may provide guidance for athlete decision strategies based on athlete trait and exercise over time. Data 900 of FIG. 9 shows an example in which resting rectus femoris muscle stiffness is greater in female than male runners. Data 1000 of FIG. 10 shows an example which demonstrates that over the course of a running season, muscle stiffness fluctuates across athletes and is associated with recent exercise and tissue loading.

Figure 11:
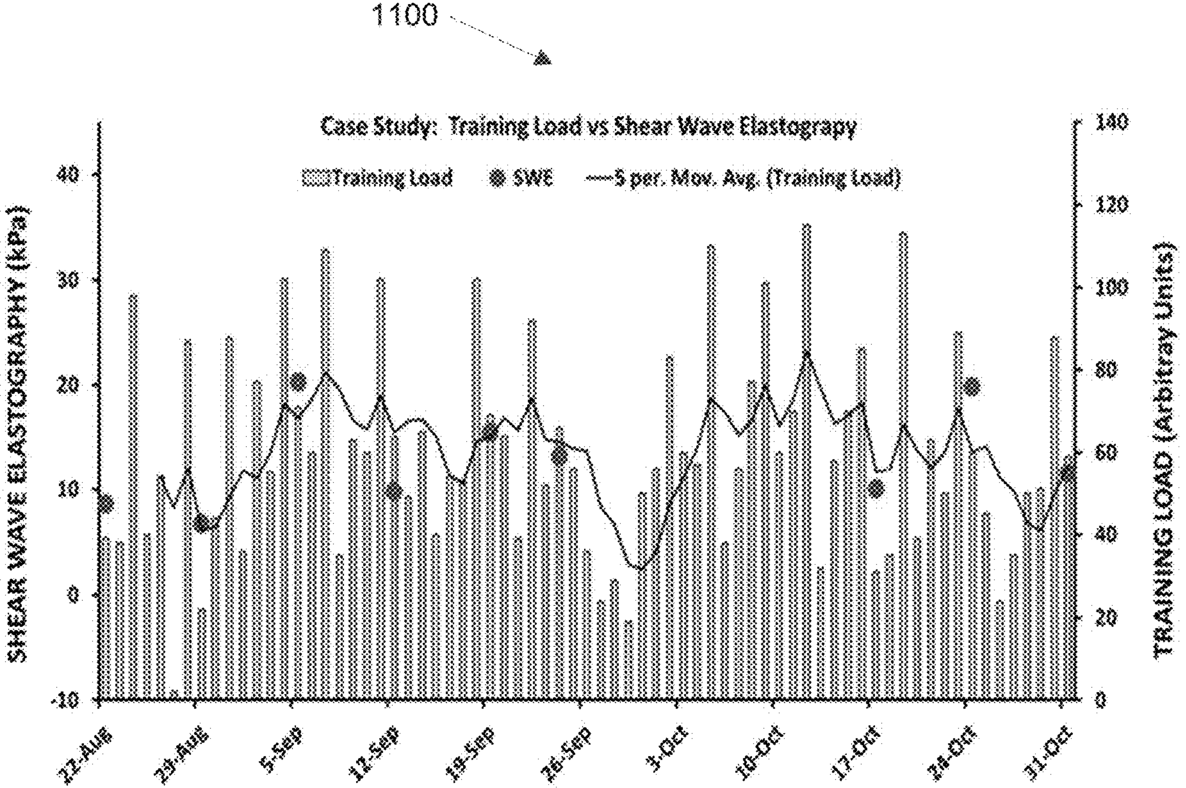

As shown in FIG. 11, shear wave elastography systems and methods of the present disclosure may provide guidance for training loaded over a period of time based on measured shear wave elastography. Similarly, shear wave elastography outputs may act as a body response indicator or performance readiness indicator, which may be used to modify future training loads in order to optimize future performance or manage injury risk or load tolerance. Data 1100 of FIG. 11 shows an example bar chart with varying daily training loads on a particular athlete or subject over a period of time, such as several days or several months. A line showing a five-day moving average of the training load is also included with data 1100. Overlaid in the same graph with data 1100 are dots indicating measured sheer wave elastography of a subject on a particular day. For example, a level of shear wave elastography measured on a given day may guide an amount of training load for the athlete on that day or on a subsequent day or days.

As shown in FIGS. 12 and 13 shear wave elastography systems and methods of the present disclosure may provide guidance for athlete decision strategies based on athlete exercise modality and muscle contraction type. Data 1200 of FIG. 12 shows an example bar chart in which changes in muscle elasticity reflect muscle involvement and specific muscle contraction type over time. For example, data 1200 demonstrates that concentric contractions of the rectus femoris muscle elicit decreases in muscle stiffness as a user progresses through several sets of a heavy exercise, whereas eccentric contractions of the rectus femoris muscle elicit increases in muscle stiffness. Data 1300 of FIG. 132 shows three example b-mode images which demonstrate that over the course of an exercise, no muscle contraction before the exercise (left image), concentric muscle contract after the exercise (center image), and eccentric muscle contraction after the exercise (right image).

Figure 14:
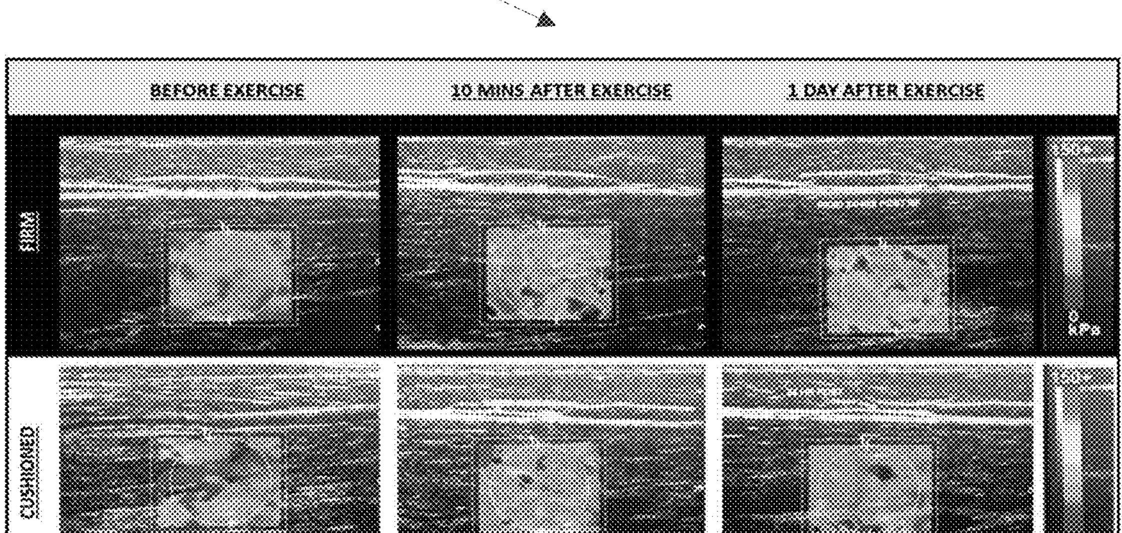
Figure 15:
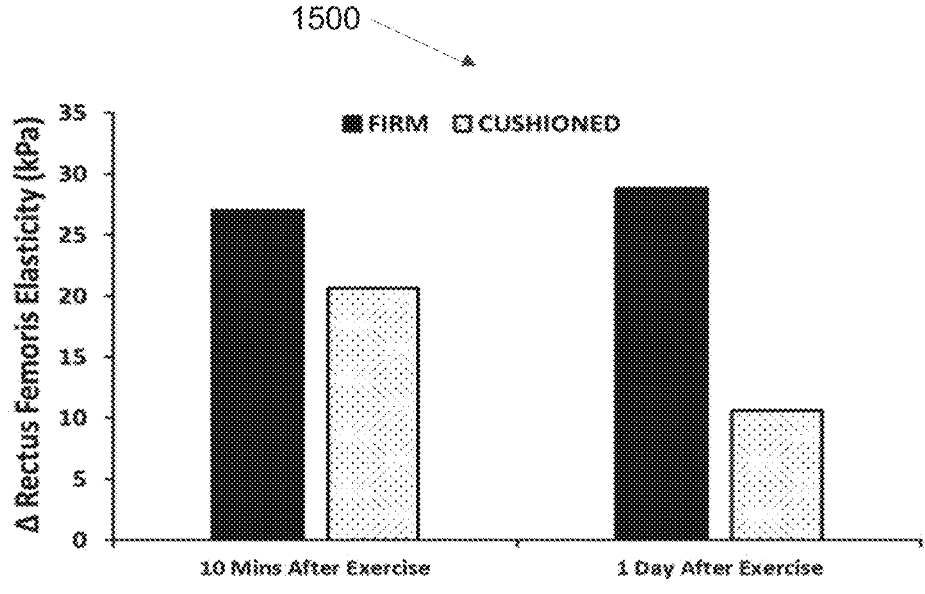

As shown in FIGS. 14 and 15, shear wave elastography systems and methods of the present disclosure may provide guidance for athlete decision strategies based on underfoot surface and cushioning during running. Specifically, FIGS. 14 and 15 demonstrate how underfoot cushioning during running may influence consequent muscle elasticity. Data 1400 of FIG. 14 shows six example b-mode images which compare a firm underfoot surface (top row of images) with a cushioned underfoot surface (bottom row of images) before an exercise (left column of images), ten minutes after the exercise (center column of images), and one day after the exercise (right column of images). Data 1500 of FIG. 15 shows an example bar chart compares changes in muscle elasticity for a firm underfoot surface and a cushioned underfoot surface over time after an exercise (that is, ten minutes after the exercise and one day after the exercise). For example, data 1500 demonstrates an increased change in muscle elasticity, indicating greater muscle stiffness, after running in the firm underfoot surface condition compared to cushioned underfoot surface condition.

Figure 16:
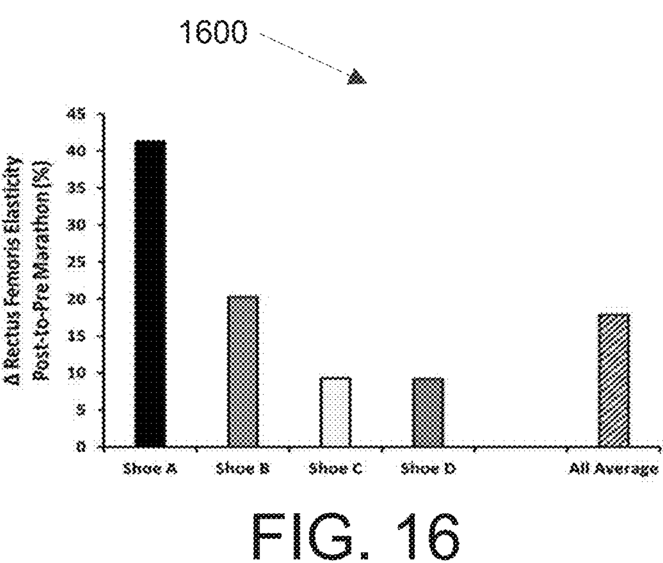
Figure 17:
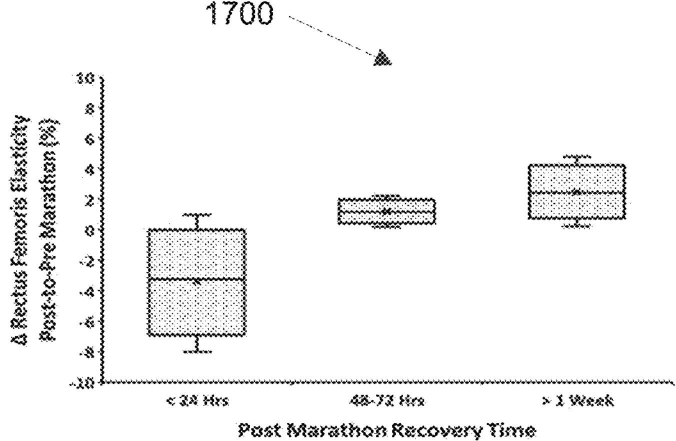
Figure 18:
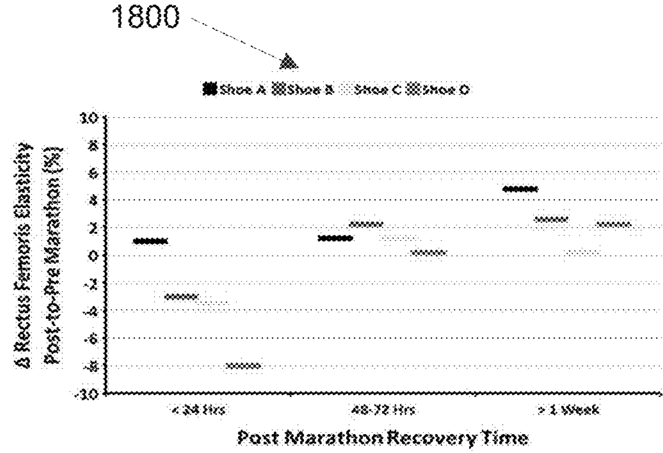

As shown in FIGS. 16, 17, and 18, shear wave elastography systems and methods of the present disclosure may provide guidance for athlete footwear decision strategies based on marathon running recovery time. Specifically, data 1600 of FIG. 16 demonstrates differing muscle elasticity changes resultant from marathon running relative to four different footwear selections. Data 1700 of FIG. 17 demonstrates that post marathon recovery time is linked to changes in muscle elasticity, such that high elasticity is associated with faster recovery. Data 1800 of FIG. 18 demonstrates, within a given post marathon recovery timeframe, differing recovery times relative to four different footwear selections.

As described herein, muscle elasticity (or, more generally, muscle stiffness or hardness) may be determined with various ultrasound shear wave elastography techniques described herein. Such techniques may serve as a non-invasive surrogate for early detection of muscle damage, muscle soreness, and/or muscle fatigue. As one particular example, accumulated microscopic muscle damage may serve as an early indicator of the onset of macro soft-tissue strain injuries and such accumulated microscopic muscle damage may be detected using the ultrasound shear wave elastography techniques described herein.

Figure 19:
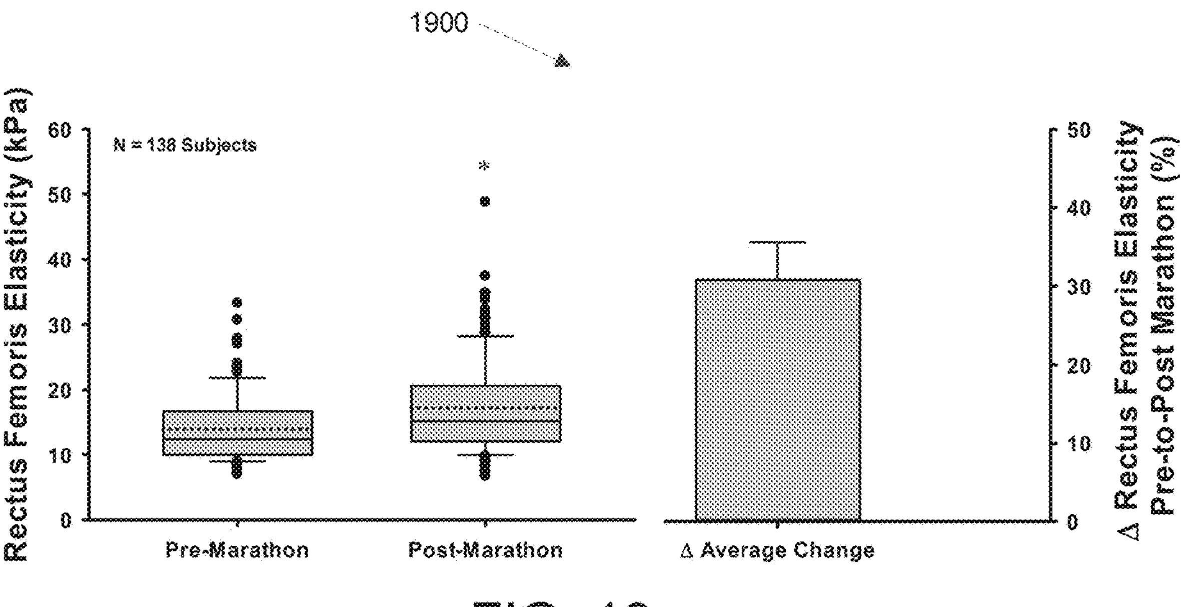

As another example, muscle elasticity may be measured in a large cohort of athletes at a particular muscle site before and after an athletic event. As shown in FIGS. 19-24, shear wave elastography systems and methods of the present disclosure may provide guidance as to the change in muscle elasticity following a particular event, such as a marathon. Specifically, FIGS. 19-24 demonstrate how rectus femoris (quadriceps) elasticity changes for a group of 138 runners following a marathon. Data 1900 of FIG. 19 shows measurements of quadriceps muscle elasticity before the marathon, after the marathon (e.g., within two hours of completing the marathon), and an average change in quadriceps muscle elasticity among the athletes. As shown by data 1900, an increase in quadriceps muscle stiffness was observed following the marathon. Specifically, muscle elasticity of the quadriceps was significantly greater (on the order of 30% greater) after the marathon.

Figure 20:
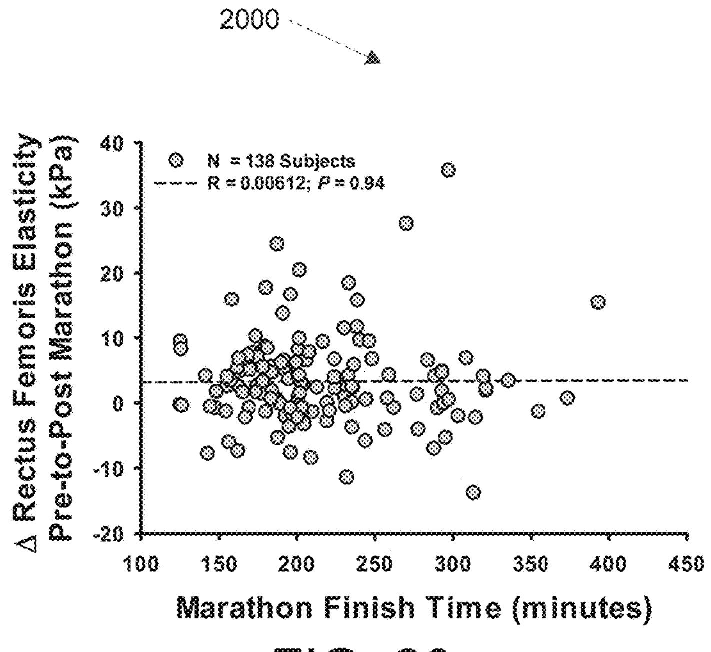

Data 2000 of FIG. 20 shows a scatterplot of marathon finish time versus change in quadriceps muscle stiffness following the marathon. As demonstrated by the low R-value (0.00612) of data 2000, runner fitness (characterized here by marathon time) may not explain a relative increase in muscle stiffness. The change in quadriceps muscle elasticity or stiffness may be assessed in combination with marathon finish time to examine the influence of fitness level on change in muscle stiffness. In this example, quadriceps muscle elasticity and marathon finish time were not significantly correlated, suggesting other factors may explain variation in muscle elasticity responses. However, in other examples, e.g., measuring change in elasticity of other muscles and/or measuring performance of a different type of athletic activity, a fitness level of an individual may be more closely correlated to an amount of change in muscle elasticity following that type of activity.

Figure 21:
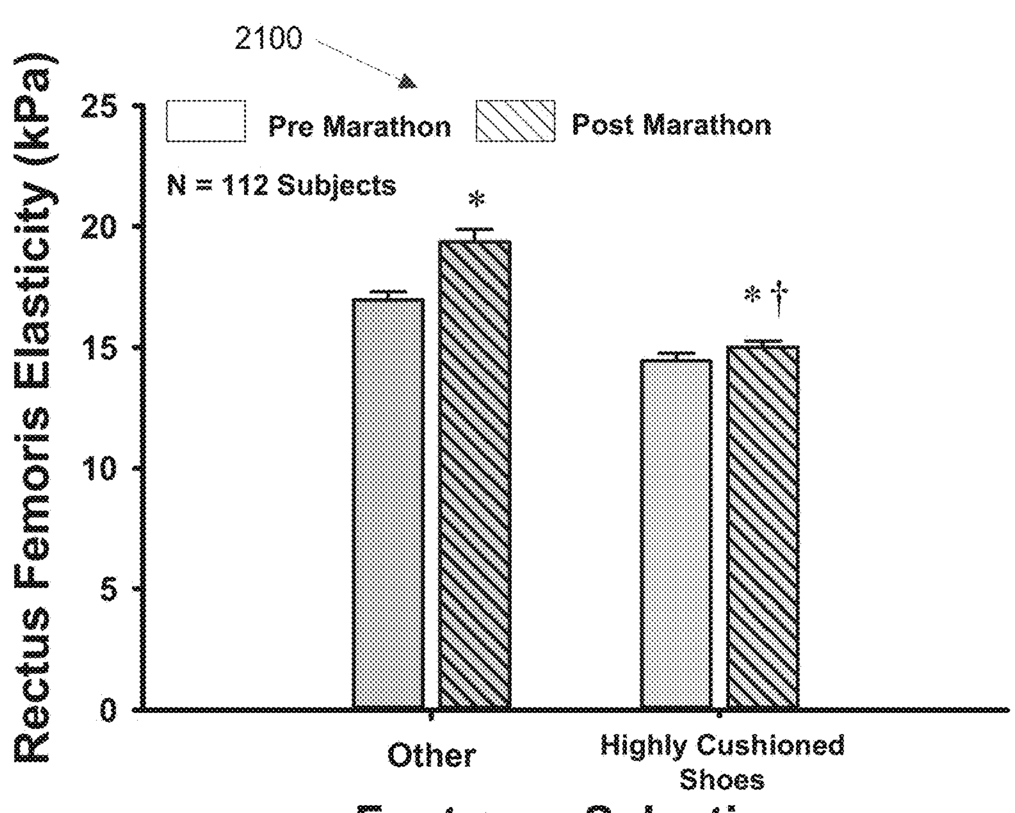
Figure 22:
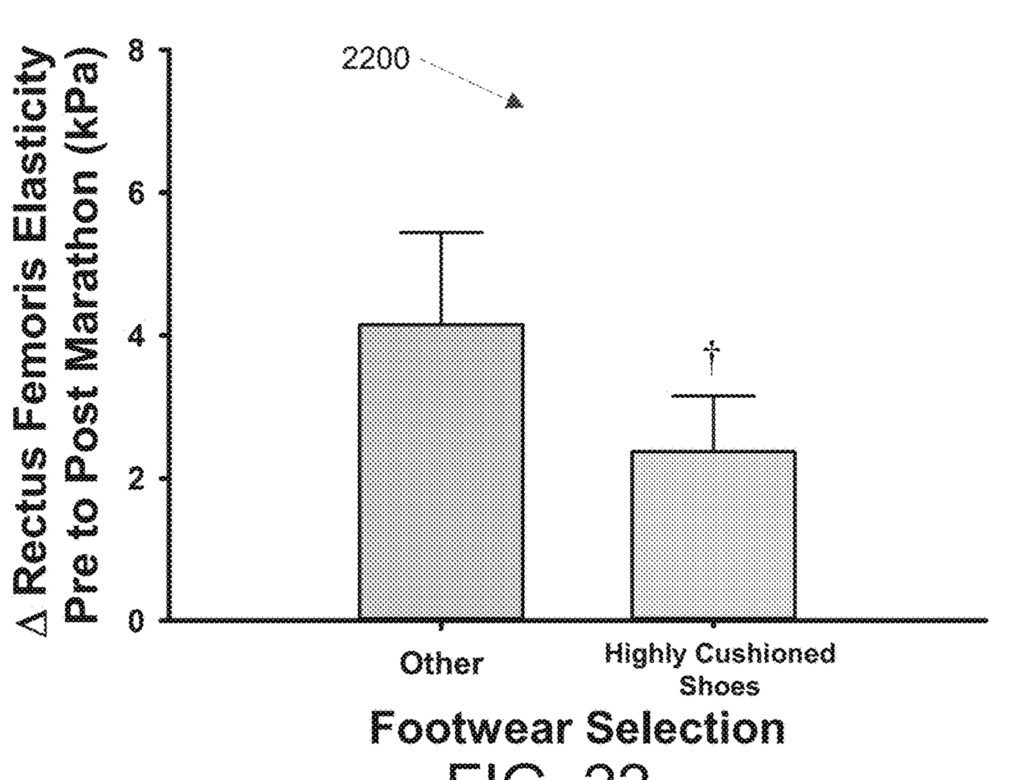

Data 2100 of FIG. 21 shows quadriceps muscle stiffness before and after the marathon for runners with two different types of footwear—"other" and "highly cushioned shoes." Similarly, data 2200 of FIG. 22 shows a change in quadriceps muscle stiffness before and after the marathon for runners with the same two different types of footwear. This example data demonstrates that the highly cushioned shoes may be linked to significantly lower muscle elasticity or muscle soreness as compared to other footwear or non-cushioned shoes. As demonstrated in this example, quadriceps muscle elasticity may be shown to increase for all or most subjects after running the marathon, but the relative change in muscle elasticity may be significantly lower for subjects who ran in highly cushioned shoes. As such, techniques described herein may be used to recommend particular types or footwear or other apparel to reduce an amount of muscle stiffness change experienced following an athletic event. Accordingly, ultrasound shear wave elastography techniques described herein may be used to experimentally assess whether particular types of footwear, apparel, athletic equipment, or other types of athletic gear may be associated with a decreased amount of muscle soreness or muscle stiffness following an athletic event, exercise session, or general athletic activity. Particular footwear or athletic apparel may thus decrease the likelihood for muscular complications of damage, soreness, fatigue, and/or strain injuries consequent to certain athletic activities by way of modulating muscle elasticity. System and methods described herein may thus include presentation of recommendations for specific types of footwear or athletic apparel based on an activity type detect changes in muscle elasticity associated with that type of activity.

Figure 23:
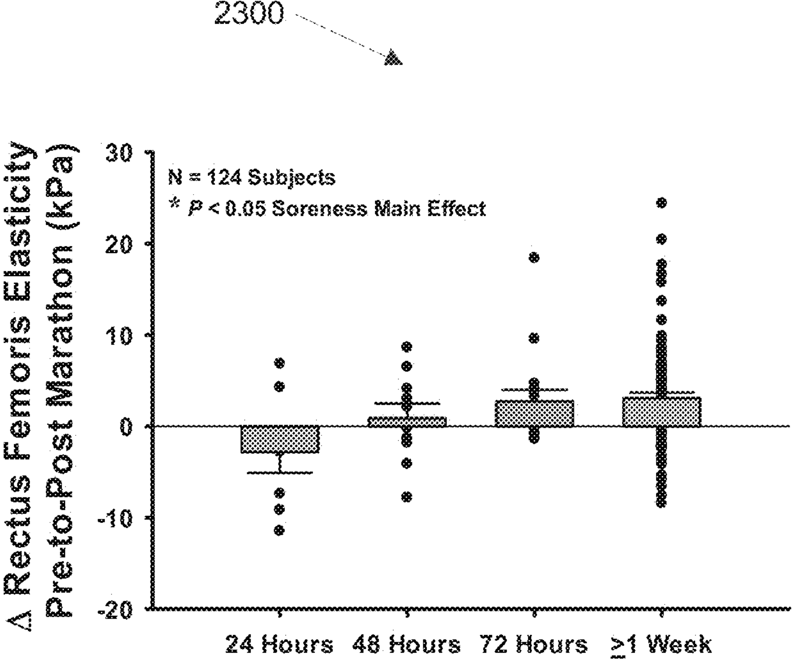
Figure 24:
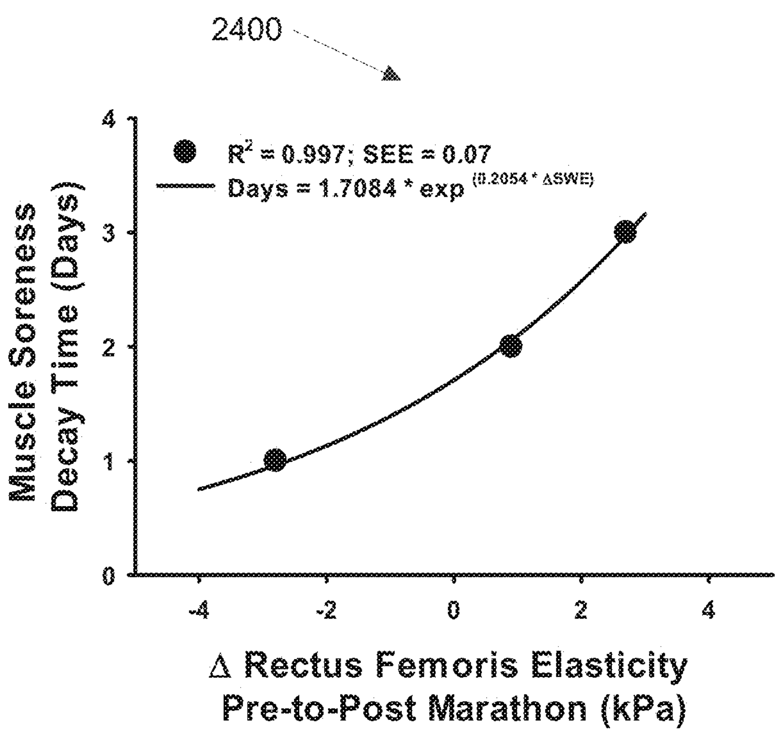

Data 2300 of FIG. 23 shows a change in quadriceps muscle stiffness over a period a time after the marathon, including 24 hours, 48 hours, 72 hours, and over 1 week after the marathon. Similarly, data 2400 of FIG. 24 shows a change in quadriceps muscle stiffness for relative to muscle soreness decay time. The change in quadriceps muscle elasticity from marathon running may be significantly related to the time by which marathon-induced muscle soreness decays. Negative to neutral changes in muscle elasticity from marathon running appear may be associated with faster decay of muscle soreness, whereas greater changes in muscle elasticity are associated with slower muscle soreness time decay. Accordingly, methods and system described herein may be used to identify interventions that can modulate muscle stiffness indices, and thus may additionally modify subsequent exercise recovery time and associated exercise training needs. This example further demonstrates that changes in quadriceps site muscle stiffness may be closely related to a muscle soreness profile, in which minor changes in muscle stiffness from marathon running may be associated with quicker decay in marathon-induced muscle soreness. Accordingly, ultrasound shear wave elastography techniques described herein may be used to experimentally assess an athlete's recovery time following an athletic event based on that athletic muscle soreness profile.

Still numerous other applications are possible for guidance based on shear wave elastography systems and methods in accordance with one or more aspects of the present disclosure. As one example, results from shear wave elastography may provide guidance for rehabilitation after tissue trauma or injury, muscle damage, tissue fatigue, force generation, and the like.

Similarly, a variety of recommendations may be made based on results from shear wave elastography described herein. Such recommendation may additionally consider data from footwear and other apparel styles, user preferences, and other related user information. For example, a user preference may include preferred styles, shoe types, and colors, and the like. A product database may be provided and may include, for example, a variety of footwear types associated with various muscle or tissue elasticity influences. As one example, a recommendation may be made for a particular type athletic shoe in the proper size for the user and with a color selection based on the user's preferences. In some embodiments, recommendations may be made to automatically fabricate custom products, such as custom footwear and custom orthotics, based on the results from shear wave elastography described herein. The size of the custom product may be determined based on the data and/or user input, while the style and/or color of the custom product may be determined based on the preference data. In this way, the recommended product may be constructed in accordance results from shear wave elastography described herein as well as user specific preferences.

One or more aspects discussed herein may be embodied in computer-usable or readable data and/or computer-executable instructions, such as in one or more program modules, executed by one or more computers or other devices as described herein. Generally, program modules include routines, programs, objects, components, data structures, and the like that perform particular tasks or implement particular abstract data types when executed by a processor in a computer or other device. The modules may be written in a source code programming language that is subsequently compiled for execution, or may be written in a scripting language such as (but not limited to) HTML or XML. The computer executable instructions may be stored on a computer readable medium such as a hard disk, optical disk, removable storage media, solid-state memory, RAM, and the like. As will be appreciated by one of skill in the art, the functionality of the program modules may be combined or distributed as desired in various embodiments. In addition, the functionality may be embodied, in whole or in part, in firmware or hardware equivalents such as integrated circuits, field programmable gate arrays (FPGA), and the like. Particular data structures may be used to more effectively implement one or more aspects discussed herein, and such data structures are contemplated within the scope of computer executable instructions and computer-usable data described herein. Various aspects discussed herein may be embodied as a method, a computing device, a system, and/or a computer program product.

Although aspects of the present disclosure have been described in certain specific aspects, many additional modifications and variations would be apparent to those skilled in the art. In particular, any of the various processes described above may be performed in alternative sequences and/or in parallel (on different computing devices) in order to achieve similar results in a manner that is more appropriate to the requirements of a specific application. It is therefore to be understood that systems, methods, and apparatuses described herein may be practiced otherwise than specifically described without departing from the scope and spirit of the present disclosure. Thus, aspects of the present disclosure as described herein should be considered in all respects as illustrative and not restrictive.

What is claimed is:

1. A computer-assisted method comprising:

receiving, by a processor, one or more data files from an ultrasound shear wave elastography apparatus configured to capture viscoelastic tissue properties in an area of a subject using ultrasound shear wave electrography;

generating a processed data file based on viscoelastic tissue parameters and one or more associated data file identifiers, wherein the one or more associated data file identifiers include at least one of: user characteristics, exercise characteristics, a footwear type, or an apparel type;

analyzing the processed data file relative to one or more other data files obtained over a period of time to assess a change in muscular elasticity in association with an athletic activity and to assess a muscle soreness profile; and generating a recommendation panel that includes a footwear recommendation, wherein the footwear recommendation is determined based on the change in muscular elasticity and based on muscular elasticity trends for the athletic activity.

2. The computer-assisted method of claim 1, wherein the one or more data files include a series of ultrasound assessment files obtained over a period of time.

3. The computer-assisted method of claim 1, further comprising:

generating an elastography report that includes an assessment of the change in muscular elasticity in association with the athletic activity and the muscle soreness profile.

4. The computer-assisted method of claim 3, wherein generating the elastography report includes identifying at least one of: an intervention exercise based on the muscle soreness profile, and one or more footwear types associated with the one or more associated data file identifiers.

5. The computer-assisted method of claim 1, wherein generating the processed data file includes computing a stiffness-to-strain parameter from a shear wave velocity obtained via ultrasound shear wave electrography.

6. The computer-assisted method of claim 1, wherein generating the processed data file includes computing a quantification of muscle elasticity values of soft tissue in the area of the subject.

7. The computer-assisted method of claim 1, wherein the viscoelastic tissue parameters include at least one of: muscle involvement, muscle contraction, muscle elasticity, rate of muscle recovery, or muscle damage.

8. The computer-assisted method of claim 1, wherein generating the recommendation panel includes determining the footwear recommendation based on a database of footwear types, each footwear type associated with a respective muscle elasticity influence.

9. The computer-assisted method of claim 1, further comprising generating an elastography map based on the processed data file.

10. The computer-assisted method of claim 9, wherein generating the elastography map includes determining mean viscoelastic tissue parameter values over the area of the subject.

11. The computer-assisted method of claim 9, wherein generating the elastography map includes providing one or more interactive elements configured to receive a user interaction to provide an interface element that displays information related to the elastography map.

12. The computer-assisted method of claim 9, wherein generating the elastography map includes providing a muscular elasticity panel that provides a trend in muscular elasticity.

13. The computer-assisted method of claim 9, wherein generating the elastography map includes determining an assessment of a change in muscular elasticity in association with muscle soreness decay time.

14. A non-transitory computer-readable medium storage medium storing computer readable instructions that, when executed, cause a processor to perform a method comprising:

receiving, by a processor, one or more data files from an ultrasound shear wave elastography apparatus configured to capture viscoelastic tissue properties in an area of a subject using ultrasound shear wave electrography;

generating a sequence of viscoelastic tissue parameters and one or more associated data file identifiers, wherein the one or more associated data file identifiers include at least one of: user characteristics, exercise characteristics, a footwear type, or an apparel type;

analyzing the sequence of viscoelastic tissue parameters and one or more associated data file identifiers relative to one or more other data files obtained over a period of time to assess a change in muscular elasticity in association with an athletic activity and to assess a muscle soreness profile; and generating a recommendation panel that includes a footwear recommendation, wherein the footwear recommendation is determined based on the change in muscular elasticity and based on muscular elasticity trends for the athletic activity.

15. The non-transitory computer-readable storage medium of claim 14, wherein processing the one or more data files includes parsing image data files and batch processing the parsed image data files to obtain the viscoelastic tissue parameters.

16. The non-transitory computer-readable storage medium of claim 14, wherein generating the footwear recommendation includes generating a report for display on a user computing device, wherein the report comprises:

an elastography map generated based on the sequence of viscoelastic tissue parameters and one or more associated data file identifiers, and one or more interactive elements configured to receive a user interaction to edit one or more data points of the elastography map or to request additional information relating to or more data points of the elastography map.

17. The non-transitory computer-readable storage medium of claim 14, wherein generating the recommendation panel includes providing one or more interactive elements configured to receive a user interaction related to a footwear purchase process of the footwear recommendation.

18. The non-transitory computer-readable storage medium of claim 14, wherein generating the recommendation panel includes generating an analysis summary generated based on one or more trends from the viscoelastic tissue parameters.

19. The non-transitory computer-readable storage medium of claim 14, wherein generating the recommendation panel includes determining the footwear recommendation based on a database of footwear types, each footwear type associated with a respective muscle elasticity influence.

20. A system comprising:

an ultrasound shear wave elastography apparatus configured to capture viscoelastic tissue properties in an area of a subject using ultrasound shear wave electrography; and an electronic device in communication with the ultrasound shear wave elastography apparatus, wherein the electronic device includes a processor and a non-transitory computer-readable storage medium storing computer-executable instructions that, when executed, cause a processor to perform a method comprising:

receiving, by the processor, one or more data files from the ultrasound shear wave elastography apparatus;

analyzing the one or more data files relative to one or more other data files obtained over a period of time to assess a change in muscular elasticity in association with an athletic activity and to assess a muscle soreness profile; and generating a recommendation panel that includes a footwear recommendation, wherein the footwear recommendation is determined based on the change in muscular elasticity and based on muscular elasticity trends for the athletic activity.

* * * * *